United States Patent
Cuccui et al.

(10) Patent No.: US 11,365,401 B2
(45) Date of Patent: *Jun. 21, 2022

(54) OLIGOSACCHARYLTRANSFERASE POLYPEPTIDE

(71) Applicant: London School of Hygiene and Tropical Medicine, London (GB)

(72) Inventors: Jon Cuccui, London (GB); Brendan Wren, London (GB)

(73) Assignee: London School of Hygiene and Tropical Medicine, London (GB)

(*) Notice: Subject to any disclaimer, the term of this patent is extended or adjusted under 35 U.S.C. 154(b) by 64 days.

This patent is subject to a terminal disclaimer.

(21) Appl. No.: 16/493,705

(22) PCT Filed: Mar. 14, 2018

(86) PCT No.: PCT/GB2018/050647
§ 371 (c)(1),
(2) Date: Sep. 12, 2019

(87) PCT Pub. No.: WO2018/167483
PCT Pub. Date: Sep. 20, 2018

(65) Prior Publication Data
US 2020/0032226 A1 Jan. 30, 2020

(30) Foreign Application Priority Data
Mar. 15, 2017 (GB) .................................. 1704117

(51) Int. Cl.
*C12N 9/10* (2006.01)
*C12N 15/74* (2006.01)
*C12P 21/00* (2006.01)

(52) U.S. Cl.
CPC ........... *C12N 9/1048* (2013.01); *C12N 15/74* (2013.01); *C12P 21/005* (2013.01)

(58) Field of Classification Search
CPC .............................. C12P 21/005; C12N 9/1048
See application file for complete search history.

(56) References Cited

U.S. PATENT DOCUMENTS

| 8,703,471 B2* | 4/2014 | Aebi | C12N 9/1048 |
| | | | 435/252.3 |
| 9,642,902 B2* | 5/2017 | Wren | C12M 23/00 |
| 10,646,562 B2* | 5/2020 | Wren | A61K 39/105 |
| 2020/0215178 A1* | 7/2020 | Wren | C12N 15/74 |

FOREIGN PATENT DOCUMENTS

| WO | WO 2009/104074 A2 | 8/2009 |
| WO | WO 2014/111724 A1 | 7/2014 |
| WO | WO 2014/114926 A1 | 7/2014 |
| WO | WO 2016/107818 A1 | 7/2016 |

OTHER PUBLICATIONS

Accession No. WP_033915694, retrieved from NCBI Accession No. RefSeq:WP_033915694, Dec. 4, 2014.
Chen et al., "Determination of the optimal aligned spacing between the Shine-Dalgarno sequence and the translation initiation codon of *Escherichia coli* mRNAs," *Nucl. Acids Res.* 22:4953-4957, 1994.
Jervis et al., "Characterization of the Structurally Diverse N-Linked Glycans of *Campylobacter* Species," *J Bacteriol* 194:2355-2362, 2012.
Terra et al., "Recent developments in bacterial protein glycan coupling technology and glycoconjugate vaccine design," *J Med Microbiol.* 61:919-926, 2012.
Combined Search and Examination Report dated Nov. 24, 2016 for Great Britain Application No. 1603948.9 (9 pages).
International Search Report and Written Opinion dated Jun. 12, 2018 for International Application No. PCT/GB2018/050647 (13 pages).

\* cited by examiner

*Primary Examiner* — Maryam Monshipouri
(74) *Attorney, Agent, or Firm* — Klarquist Sparkman, LLP

(57) ABSTRACT

The disclosure relates to an oligosaccharyltransferase polypeptides and their use in the synthesis of glycoconjugates in bacterial cells; vaccines and immunogenic compositions comprising said glycoconjugates and their use in the prevention and/or treatment of bacterial infection. Bacterial expression system comprising said oligosaccharyltransferase polypeptides are also disclosed.

27 Claims, 2 Drawing Sheets
Specification includes a Sequence Listing.

OLIGOSACCHARYLTRANSFERASE POLYPEPTIDE

CROSS REFERENCE TO RELATED APPLICATIONS

This is the U.S. National Stage of International Application No. PCT/GB2018/050647, filed Mar. 14, 2018, which was published in English under PCT Article 21(2), which in turn claims the benefit of Great Britain Application No. 1704117.9, filed Mar. 15, 2017.

FIELD OF THE INVENTION

The disclosure relates to an oligosaccharyltransferase polypeptide and its use in the synthesis of glycoconjugates in bacterial cells; vaccines and immunogenic compositions comprising said glycoconjugates and their use in the prevention and/or treatment of bacterial infection. Bacterial expression systems comprising said oligosaccharyltransferases are also disclosed. We also disclose a modified oligosaccharyltransferase polypeptide that has altered glycan specificity and/or enhanced enzyme activity when compared to the unmodified oligosaccharyltransferase polypeptide.

BACKGROUND OF THE INVENTION

Vaccines or immunogenic compositions comprising glycan antigens can induce the production of specific antibodies to provide protection against a variety of pathogenic bacteria. Subunit vaccines are typically preferred over inactivated or attenuated pathogens as they often exhibit lower side effects; however, the immunogenicity of subunit vaccines is frequently low and typically fails to generate sufficient memory B-cell response. The coupling of a polysaccharide antigen to a protein carrier, so generating a glycoconjugate, is known to increase the immunogenicity significantly. Currently licensed human glycoconjugate vaccines include those against *Haemophilus influenzae, Neisserria meningitidis* and *Streptococcus pneumonia*.

The development and chemical synthesis of glycoconjugate vaccines is laborious and costly requiring several steps including the purification of polysaccharide glycan from the native pathogen and the chemical coupling of the sugar to a suitable protein carrier. The use of organic systems represents often a more rapid and economical method for the production of glycoconjugates. *Campylobacter jejuni* harbours a gene cluster involved in the synthesis of lipo-oligosaccharides and N-linked glycoproteins involved in the glycosylation of over 30 proteins. The oligosaccharyltransferase PglB identified in *C. jejuni*, the enzyme responsible for the transfer of glycans to protein acceptor proteins and part of the gene cluster, was also found to catalyse the transfer of glycans onto a wide range of different non-species related protein acceptors.

Production of glycoconjugate vaccines in a bacterial system such as *E. coli* utilising PglB, a carrier polypeptide and an antigenic saccharide is disclosed in WO2009/104074. A further oligosaccharyltransferase isolated from the related species *Campylobacter sputorum* with glycan transfer capability is disclosed in WO2014/111724.

The production of glycoconjugates in a bacterial expression system requires the co-expression of three genes ["tri-plasmid"]: an acceptor protein, a polysaccharide biosynthetic locus and an oligosaccharyltransferase enzyme. WO2014/111724 discloses a method providing the stable integration of the genes encoding the acceptor protein, a glycan biosynthetic locus and an oligosaccharyltransferase into a bacterial genome using transposable elements for the production of glycoconjugates at reasonable levels.

This disclosure relates to the identification of an alternative *C. sputorum* oligosaccharyltransferase closely related in sequence to the oligosaccharyltransferase disclosed in WO2014/111724 which has enhanced glycan transfer activity when compared to closely homologous oligosaccharyltransferases. Moreover, recombinant expression systems with decreased translational efficiency comprising oligosaccharyltransferases, toxic carrier proteins or genes encoding proteins required for glycan biosynthesis are also disclosed. Translational efficiency is decreased by providing a vector with increased distance between the ribosome binding site [RBS] and the translational start codon thus enabling bacterial growth to a high density and avoiding deleterious effects of expressing recombinant proteins at concentrations which are toxic to the bacterial cell. Furthermore, the disclosure relates to the characterisation of a modified oligosaccharyltransferase polypeptide with altered glycan specificity and/or enzyme activity when compared to the unmodified oligosaccharyltransferase polypeptide.

STATEMENTS OF THE INVENTION

According to an aspect of the invention there is provided a transcription cassette comprising:
  i) a nucleic acid molecule comprising a nucleotide sequence that encodes a oligosaccharyltransferase polypeptide as set forth in SEQ ID NO: 1 or 2; or
  ii) a nucleic acid molecule comprising a nucleotide sequence that is degenerate to the nucleotide sequence set forth in SEQ ID NO: 1 or 2 and encodes a polypeptide comprising an amino acid sequence as set forth in SEQ ID NO: 3; or
  iii) a nucleic acid molecule comprising a nucleotide sequence that encodes an oligosaccharyltransferase polypeptide wherein said nucleotide sequence is at least 97% identical to the nucleotide sequence set forth in SEQ ID NO: 1; or
  iv) a nucleic acid molecule comprising a nucleotide sequence that encodes an oligosaccharyltransferase polypeptide wherein said nucleotide sequence is at least 77% identical to the nucleotide sequence set forth in SEQ ID NO: 2.

wherein said nucleic acid molecule is operably linked to a promoter adapted for expression in a bacterial host cell.

In a preferred embodiment of the invention said nucleic acid molecule comprises a nucleotide sequence that is 98% or 99% identical to the nucleotide sequence set forth in SEQ ID NO: 1.

In an alternative embodiment of the invention said nucleic acid molecule comprises a nucleotide sequence that is at least 78%, 79%, 80%, 81%, 82%, 83%, 84%, 85%, 86%, 87%, 88%, 89%, 90%, 91%, 92%, 93%, 94%, 95%, 96%, 97% identical to the nucleotide sequence set forth in SEQ ID NO: 2.

In a preferred embodiment of the invention there is provided a transcription cassette comprising a nucleic acid molecule encoding an oligosaccharyltransferase wherein said oligosaccharyltransferase comprises an amino acid sequence that is 97% identical to the amino acid sequence set forth in SEQ ID NO: 3.

Preferably, said oligosaccharyltransferase comprises an amino acid sequence that is 98% or 99% identical to the amino acid sequence set forth in SEQ ID NO: 3.

In a preferred embodiment of the invention said transcription cassette further comprises a nucleic acid molecule encoding a carrier polypeptide wherein said carrier polypeptide comprises one or more glycosylation motifs for said oligosaccharyltransferase.

In a further preferred embodiment of the invention said transcription cassette further or alternatively comprises a nucleic acid molecule comprising a nucleotide sequence encoding a biosynthetic locus comprising one or more polypeptides required for the synthesis of a heterologous glycan antigen.

In a preferred embodiment of the invention said oligosaccharyltransferase and/or said carrier polypeptide and/or biosynthetic locus is operably linked to a regulatable promoter to provide regulated expression of each or all nucleic acid molecules encoding said polypeptides.

In a preferred embodiment of the invention said one or more polypeptides required for the synthesis of a heterologous glycan antigen are operably linked to one or more regulatable promoters to provide regulated expression of each or all nucleic acid molecules encoding said polypeptides.

In a preferred embodiment of the invention said promoter includes an inducible nucleotide element conferring regulated expression in response to an inducer.

In an alternative embodiment of the invention said promoter includes a repressible nucleotide element conferring regulated expression in response to a repressor.

In a preferred embodiment of the invention said promoter is further operably linked to a ribosome binding site wherein there is provided a nucleotide spacer sequence between the 3' prime end of said ribosome binding site and the 5' initiating start codon of the nucleic acid molecule encoding said oligosaccharyltransferase wherein translation from the nucleic acid molecule encoding said oligosaccharyltransferase is reduced when compared to a control nucleic acid molecule encoding said recombinant polypeptide that does not comprise said nucleotide spacer sequence.

In a further preferred embodiment said oligosaccharyltransferase comprises a sequence as set forth in SEQ ID NO 1, 2 or 18.

In a preferred embodiment of the invention said promoter is further operably linked to a ribosome binding site wherein there is provided a nucleotide spacer sequence between the 3' prime end of said ribosome binding site and the 5' initiating start codon of the nucleic acid molecule encoding said carrier polypeptide wherein translation from the nucleic acid molecule encoding said carrier polypeptide is reduced when compared to a control nucleic acid molecule encoding said recombinant polypeptide that does not comprise said nucleotide spacer sequence.

In a preferred embodiment of the invention said carrier polypeptide includes the amino acid motif: Asn-X-Ser or Asn-X-Thr where X is any amino acid except proline.

In an alternative embodiment of the invention said carrier polypeptide includes the amino acid motif: D/E-X-N-X-S/T (SEQ ID NO: 46), wherein X is any amino acid except proline.

In an alternative preferred embodiment of the invention said carrier polypeptide includes the amino acid motif D/E-X-N-X-S/T (SEQ ID NO: 46), wherein X is any amino acid except proline and is selected from the group consisting of: DVNVT (SEQ ID NO 19), EVNAT(SEQ ID NO 20), DQNAT(SEQ ID NO 21), DNNNT(SEQ ID NO 22), DNNNS (SEQ ID NO 23), DQNRT (SEQ ID NO 24), ENNFT(SEQ ID NO 25), DSNST(SEQ ID NO 26), DQNIS (SEQ ID NO 27), DQNVS (SEQ ID NO 28), DNNVS (SEQ ID NO 29), DYNVS (SEQ ID NO 30), DFNVS (SEQ ID NO 31), DFNAS (SEQ ID NO 32), DFNSS (SEQ ID NO 33), DVNAT(SEQ ID NO 34), DFNVT (SEQ ID NO 35) or DVNAS (SEQ ID NO 36).

In a further preferred embodiment said carrier polypeptide comprises a nucleic acid encoding said polypeptide comprising a nucleotide sequence as set forth in SEQ ID NO: 4 or 6 or 8.

In a preferred embodiment of the invention said promoter is further operably linked to a ribosome binding site wherein there is provided a nucleotide spacer sequence between the 3' prime end of said ribosome binding site and the 5' initiating start codon of the nucleic acid molecule encoding said one or more polypeptides required for the synthesis of a heterologous glycan antigen wherein translation from the nucleic acid molecule encoding said biosynthetic locus is reduced when compared to a control nucleic acid molecule encoding said recombinant polypeptide that does not comprise said nucleotide spacer sequence.

In a preferred embodiment of the invention said heterologous glycan antigen is a heptasaccharide.

In a preferred embodiment of the invention said biosynthetic locus is the Pgl locus.

Preferably said Pgl locus comprises genes encoding said one or more polypeptides selected from the group consisting of: PglG, PglF, PglE, optionally Cj1122c; PglD, PglC, PglA, PglJ, PglI, PglH, PglK, Gne In a further preferred embodiment of the invention said nucleic acid molecule encoding one or more polypeptides required for the synthesis of a heterologous glycan antigen comprises a nucleotide sequence as set forth in SEQ ID NO: 10, wherein said SEQ ID NO 10 does not include a functional version of PglB (SEQ ID NO: 18).

Ribosome Binding Sites [RBS] in prokaryotic nucleic acid molecules are referred as a Shine Dalgarno [SD] sequence and is a consensus sequence that is typically positioned 5-13 nucleotides upstream of an initiating codon of the nucleic acid molecule. The consensus RBS sequence consists of a purine rich region followed by an A and T-rich translational spacer region, for example the consensus AGGAGG or AGGAGGU. Initiating codons are commonly AUG but translation can also be initiated at codons such as GUG, UUG, AUU or CUG.

In a preferred embodiment of the invention said nucleotide spacer sequence is at least 13 nucleotides in length.

In a preferred embodiment of the invention said nucleotide spacer sequence is 13 and 40 nucleotides in length; preferably the nucleotide spacer sequence is between 13 and 20 nucleotides in length.

In a preferred embodiment of the invention said nucleotide spacer sequence is 16 nucleotides in length.

In a preferred embodiment of the invention said nucleotide spacer sequence is 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

In a preferred embodiment of the invention said nucleotide spacer sequence is at least 40 nucleotides in length.

In a preferred embodiment of the invention said nucleotide spacer sequence is between 40 and 75 nucleotides in length.

In a preferred embodiment of the invention said nucleotide spacer sequence is 40, 45, 50, 55, 60, 65, 70 or 75 nucleotides in length.

In an alternative embodiment of the invention the reduction in nucleic acid molecule translation of said oligosaccharyltransferase and/or said carrier polypeptide and/or biosynthetic locus is reduced by at least 10% when compared to a control nucleic acid molecule that encodes said oligosaccharyltransferase and/or said carrier polypeptide and/or biosynthetic locus but does not comprise said spacer nucleotide sequence.

In a preferred embodiment of the invention the reduction in nucleic acid translation is 15%, 20%, 25%, 30%, 35%, 40%, 45%, 50%, 55%, 60%, 65%, 70%, 75%, 80%, 85% or 90% when compared to a control nucleic acid that encodes said recombinant polypeptide but does not comprise said spacer nucleotide sequence.

Bacterial expression systems that utilize inducers and repressors of gene expression are well known in the art and include modifications that are well established which enhance induction or repression of gene expression. For example is lacIq carries a mutation in the promoter region of the lacI gene that results in increased transcription and higher levels of Lac repressor within the cells. Moreover, the Ptac, a strong hybrid promoter composed of the −35 region of the trp promoter and the −10 region of the lacUV5 promoter/operator and is strongly inducible.

Alternative heterologous glycan antigens include O-antigen. O-antigens comprising repetitive glycan polymers are the polysaccharide component of lipopolysaccharides (LPS) found associated with the outer membrane of gram negative bacteria. O-antigens typically elicit a strong immune response in animals. The composition of the 0 chain varies from bacterial strain to bacterial strain. For example there are over 160 different O-antigen structures known produced by different *E. coli* strains. O-antigens are exposed on the outer surface of the bacterial cell, and serve a target for recognition by host antibodies. Examples of polysaccharide synthesis loci are well known in the art and can be found in: "Genetic analysis of the capsular biosynthetic locus from all 90 pneumococcal serotypes", Bentley S D, Aanensen D M, Mavroidi A, Saunders D, Rabbinowitsch E, Collins M, Donohoe K, Harris D, Murphy L, Quail M A, Samuel G, Skovsted I C, Kaltoft M S, Barrell B, Reeves P R, Parkhill J, Spratt B G. PLoS Genet. 2006 March: 2 (3):e31; "Gene content and diversity of the loci encoding biosynthesis of capsular polysaccharides of the 15 serovar reference strains of *Haemophilus parasuis*." Howell K J, Weinert L A, Luan S L, Peters S E, Chaudhuri R R, Harris D, Angen O, Aragon V, Parkhill J, Langford P R, Rycroft A N, Wren B W, Tucker A W, Maskell D J; BRaDP1T Consortium. J Bacteriol. 2013 September: 195(18):4264-73. doi: 10.1128/JB.00471-13. Epub 2013 Jul. 19; "Exploitation of bacterial N-linked glycosylation to develop a novel recombinant glycoconjugate vaccine against *Francisella tularensis*". Cuccui J, Thomas R M, Moule M G, D'Elia R V, Laws T R, Mills D C, Williamson D, Atkins T P, Prior J L, Wren B W. Open Biol. 2013 May 22; 3(5):130002; and "Characterization of the structurally diverse N-linked glycans of *Campylobacter* species". Jervis A J, Butler J A, Lawson A J, Langdon R, Wren B W, Linton D. J Bacteriol 2012 May: 194(9):2355-62.

According to a further aspect of the invention there is provided an oligosaccharyltransferase polypeptide selected from the group:
i) a nucleic acid molecule comprising a nucleotide sequence that encodes a oligosaccharyltransferase polypeptide as set forth in SEQ ID NO: 1 or 2; or
ii) a nucleic acid molecule comprising a nucleotide sequence that is degenerate to the nucleotide sequence set forth in SEQ ID NO: 1 or 2 and encodes a polypeptide comprising an amino acid sequence as set forth in SEQ ID NO: 3; or iii) a nucleic acid molecule comprising a nucleotide sequence that encodes an oligosaccharyltransferase polypeptide wherein said nucleotide sequence is at least 97% identical to the nucleotide sequence set forth in SEQ ID NO: 1; or
iv) a nucleic acid molecule comprising a nucleotide sequence that encodes an oligosaccharyltransferase polypeptide wherein said nucleotide sequence is at least 77% identical to the nucleotide sequence set forth in SEQ ID NO: 2, wherein said oligosaccharyltransferase is for use in the transfer of one or more heterogeneous glycans to at least one carrier polypeptide.

In a preferred embodiment of the invention said nucleic acid molecule comprises a nucleotide sequence that is 98% or 99% identical to the nucleotide sequence set forth in SEQ ID NO: 1.

In an alternative embodiment of the invention said nucleic acid molecule comprises a nucleotide sequence that is at least 78%, 79%, 80%, 81%, 82%, 83%, 84%, 85%, 86%, 87%, 88%, 89%, 90%, 91%, 92%, 93%, 94%, 95%, 96%, 97% identical to the nucleotide sequence set forth in SEQ ID NO: 2.

In a preferred embodiment of the invention there is provided a transcription cassette comprising a nucleic acid molecule encoding an oligosaccharyltransferase wherein said oligosaccharyltransferase comprises an amino acid sequence that is at least 97% identical to the amino acid sequence set forth in SEQ ID NO: 3.

Preferably, said oligosaccharyltransferase comprises an amino acid sequence that is 98% or 99% identical to the amino acid sequence set forth in SEQ ID NO: 3.

In a preferred embodiment of the invention said use is in a microbial host cell and said oligosaccharyltransferase polypeptide is transformed into said microbial host cell.

According to a further aspect of the invention there is provided a vector comprising a transcription cassette according to the invention.

In a preferred embodiment of the invention said vector is a plasmid.

In an alternative preferred embodiment of the invention said vector is a transposon.

In a preferred embodiment of the invention said transposon is selected from the group consisting of: Tn5, Tn10, Himar1 and other mariner elements, Tn7, Tn917 and Tn916.

In a preferred embodiment of the invention said transposon is Tn5.

According to a further aspect of the invention there is provided a bacterial cell genetically modified with a transcription cassette or vector according to the invention.

In a preferred embodiment of the invention said nucleic acid molecule encoding said oligosaccharyltransferase is stably integrated into the genome of said bacterial cell.

In a further preferred embodiment of the invention said nucleic acid molecule encoding said carrier polypeptide is stably integrated into the genome of said bacterial cell.

In a yet further preferred embodiment of the invention said nucleic acid molecule encoding said biosynthetic locus is stably integrated into the genome of said bacterial cell.

Genetic transformation of an attenuated pathogenic bacterial cell according to the invention using a transcription cassette as herein disclosed can be via transformation using episomal vectors that are replicated separately from the genome of the attenuated pathogenic bacterial cell to provide multiple copies of a gene or genes. Alternatively, integrating vectors that recombine with the genome of the attenuated pathogenic bacterial cell and which is replicated with the genome of said attenuated pathogenic bacterial cell.

In a preferred embodiment of the invention said nucleic acid molecule encoding a oligosaccharyltransferase polypeptide, a carrier polypeptide and a biosynthetic locus comprising one or more polypeptides required for the synthesis of a heterologous glycan antigen are each integrated into the genome of said bacterial cell.

In a preferred embodiment of the invention said bacterial cell is a pathogenic Gram-positive bacterial cell.

In a preferred embodiment of the invention said bacterial cell is a pathogenic Gram-negative bacterial cell.

In a preferred embodiment of the invention said bacterial cell is a human pathogen.

In a preferred embodiment of the invention said human pathogen is selected from the group: *Neisseria, Moraxella, Escherichia, Salmonella, Shigella, Pseudomonas, Helicobacter, Legionella, Haemophilus, Klebsiella, Enterobacter, Cronobacter* and *Serratia*.

In a preferred embodiment of the invention said bacterial cell is a non-human pathogen.

In a preferred embodiment of the invention said non-human pathogen is selected from group: *Mannheimia* spp., *Actinobacillus* spp. e.g *Actinobacillus pleuropneumoniae, Pasteurella* spp., *Haemophilus* spp. or *Edwardsiella* spp.

In a preferred embodiment of the invention said bacterial cell is a zoonotic bacterial species. In a preferred embodiment of the invention said zoonotic bacterial species is selected from the group: *Brucella* spp., *Campylobacter* spp., *Vibrio* spp., *Yersinia* spp. and *Salmonella* spp.

According to a further aspect of the invention there is providing a bacterial cell culture comprising a genetically modified bacterial cell according to the invention.

According to an aspect of the invention there is provided a transcription cassette or vector according to the invention for use in the production of one or more glycoconjugates.

According to a further aspect of the invention there is provided a process for the production of one or more glycoconjugates comprising:
i) providing a bacterial cell culture according to the invention;
ii) providing cell culture conditions; and
iii) isolating one or more glyconjugates from the bacterial cell or cell culture medium.

According to a further aspect of the invention there is provided a cell culture vessel comprising a bacterial cell culture according to the invention.

In a preferred embodiment of the invention said cell culture vessel is a fermentor.

Bacterial cultures used in the process according to the invention are grown or cultured in the manner with which the skilled worker is familiar, depending on the host organism. As a rule, bacteria are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batchwise, semi-batchwise or continuously. Nutrients can be provided at the beginning of the fermentation or fed in semi-continuously or continuously. The products produced can be isolated from the bacteria as described above by processes known to the skilled worker, for example by extraction, distillation, crystallization, if appropriate precipitation with salt, and/or chromatography. In this process, the pH value is advantageously kept between pH 4 and 12, preferably between pH 6 and 9, especially preferably between pH 7 and 8.

An overview of known cultivation methods can be found in the textbook Bioprocess technology 1. Introduction to Bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Brunswick/Wiesbaden, 1994)).

The culture medium to be used must suitably meet the requirements of the bacterial strains in question. Descriptions of culture media for various bacteria can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogenphosphate or dipotassiumhydrogenphosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for culturing bacteria usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C. and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

According to a further aspect of the invention there is provided a process for the identification of novel glycoconjugates comprising:
i) forming a cell culture preparation comprising a bacterial cell and a transposon according to the invention;
ii) incubating the preparation to allow stable integration of the transposon;
iii) selecting bacterial cells that have stably integrated the transposon using culture conditions that select for bacterial cells that are stable integrants;
iv) cloning bacterial cells that have stably integrated the transposon;
v) isolating glycoconjugates from the cloned bacterial cells or cell culture medium; and
vi) analysing the monosaccharide or polysaccharide content of said isolated glycoconjugate.

According to a further aspect of the invention there is provided a glycoconjugate formed by the process according to the invention.

According to an aspect of the invention there is provided an isolated oligosaccharyltransferase polypeptide wherein the polypeptide comprises an amino acid sequence set forth in SEQ ID NO: 3, or polymorphic sequence variant thereof, wherein the amino acid sequence is modified by deletion or substitution of at least one amino acid residue and said modified polypeptide has altered substrate specificity and/or increased oligosaccharyltransferase activity when compared to an unmodified oligosaccharyltransferase polypeptide comprising the amino acid sequence set forth in SEQ ID NO: 3.

In a preferred embodiment of the invention said modification is a deletion or substitution of one or more of the amino acid residues selected from the group consisting of amino acid residue 86 and/or amino acid residue 293 and/or amino acid residue 316 as set forth in SEQ ID NO: 3.

In a preferred embodiment of the invention said modification is amino acid substitution wherein the substitution is amino acid residue 86 as set forth in SEQ ID NO: 3 wherein amino acid residue serine is substituted with amino acid residue arginine.

In an alternative embodiment of the invention said modification is amino acid substitution wherein the substitution is amino acid residue 293 as set forth in SEQ ID NO: 3 wherein amino acid residue asparagine is substituted with amino acid residue proline.

In a further alternative embodiment of the invention said modification is amino acid substitution wherein the substitution is amino acid residue 316 as set forth in SEQ ID NO: 3 wherein amino acid residue asparagine is substituted with amino acid residue valine.

In a preferred embodiment of the invention said modified polypeptide or polymorphic sequence variant comprises the amino acid sequence set forth in SEQ ID NO: 43.

In a further preferred embodiment of the invention said modified nucleic acid sequence encodes a polypeptide comprising a sequence set forth in SEQ ID NO 43.

According to an aspect of the invention there is provided an isolated nucleic acid molecule that encodes a polypeptide according to the invention.

In a preferred embodiment of the invention said isolated nucleic acid molecule is selected from the group consisting of:
i) a nucleic acid molecule comprising or consisting of the nucleotide sequence as set forth in SEQ ID NO: 42;
ii) a nucleic acid molecule comprising or consisting of a nucleotide sequence that is degenerate to the nucleotide sequence set forth in SEQ ID NO: 42 and encodes a polypeptide comprising the modified amino acid sequence according to the invention.

In a preferred embodiment of the invention said isolated nucleic acid molecule comprises or consists of the nucleotide sequence set forth in SEQ ID NO: 42.

In a preferred embodiment of the invention said nucleic acid molecule is part of a transcription cassette.

According to an aspect of the invention there is provided a vector comprising a nucleic acid molecule according to the invention.

In a preferred embodiment of the invention said vector is an expression vector.

In a preferred embodiment of the invention said vector is a transposon.

According to a further aspect of the invention there is provided a cell transformed or transfected with a nucleic acid molecule or expression vector according to the invention.

In a preferred embodiment of the invention said cell is a microbial cell, for example a bacterial cell.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figures;

BRIEF SUMMARY OF THE DRAWINGS

FIG. 1B shows growth of *E. coli* CLM24 cells without any induction of protein expression (no IPTG or L-arabinose was added). We found that CspglB2 and *C. jejuni* pglB appeared to have very similar toxicity levels;

SEQUENCE LISTING

Figure 1A:
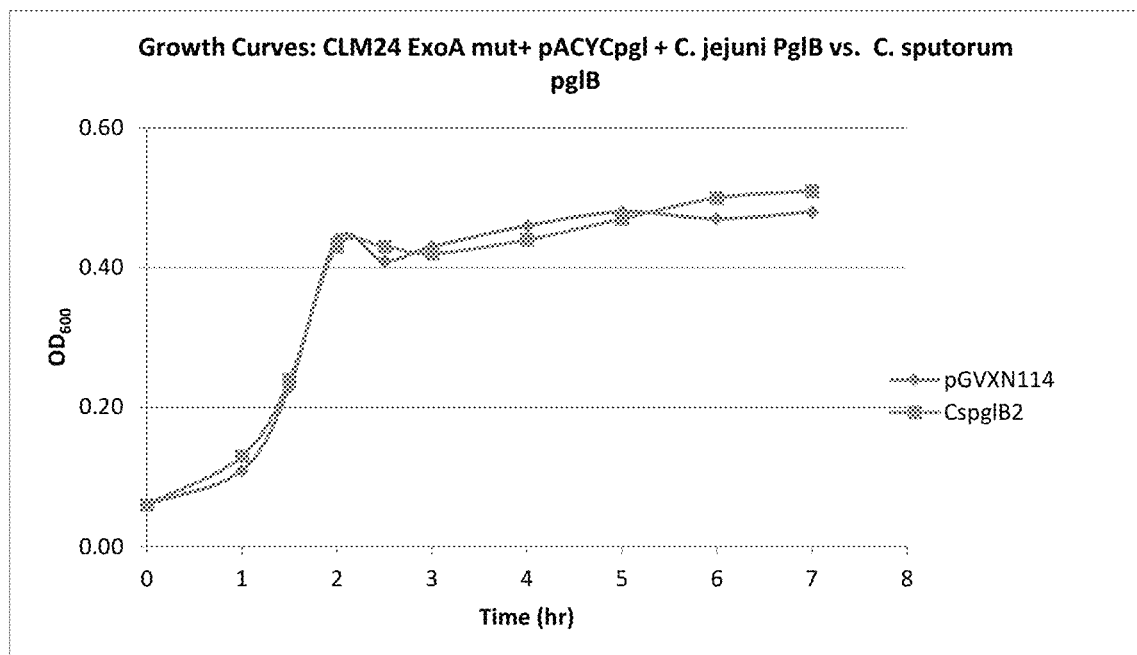
FIGS. 1A and 1B illustrate a growth comparison in *E. coli* CLM24 following induction of expression of *C. jejuni* pglB and CspglB2. Growth curves were set up to monitor the optical density of the *E. coli* cells following induction of CjpglB or CspglB2 (FIG. 1A).

The Sequence Listing is submitted as an ASCII text file in the form of the file named "Sequence.txt" (~96 kb), which was created on Sep. 2, 2019, and which is incorporated by reference herein.

MATERIALS & METHODS

Construction of *C. sputorum* pglB2 Expression Plasmid pELLA1

A codon optimised version of *C. sputorum* pglB2 was generated by DNA synthesis in the cloning vector pUC57 km and designed to have EcoRI (GAATTC) restriction enzyme sites at the 5' and 3' end of the construct. The plasmid pEXT21 was grown in *E. coli* DH5α cells and purified by plasmid extraction (QIAGEN Ltd UK). 1 μg of pUC57Km containing CsPglB2 and 1 μg of pEXT21 were digested with EcoRIHF (New England Biolabs U.K.) cloned into the EcoRI site of the IPTG inducible expression vector pEXT21 to generate the vector pELLA1.

Construction of pELLA2

The gene coding for *C. sputorum* PglB2 was amplified by PCR with the pTac promoter and LacI repressor from plasmid pEXT21 as a template using accuprime Taq hifi with (SEQ ID NO: 11: 5'-TTTTGCGGCCGCTTCTACGTGTTCCGCTTCC-3') as forward primer and (SEQ ID NO: 12: 5'-TTTTGCGGCCGCATTGCGTTGCGCTCACTGC-3') reverse primer using the following cycling conditions, 94° C./2 minutes followed by 35 cycles of 94° C. for 30 seconds, 56° C. for 30 seconds and 68° C. for 4 minutes, and ligated into the unique NotI site in pJCUSA1 a Zeocin® resistant transposon where the antibiotic marker is flanked by loxP sites allowing for downstream removal of antibiotic marker from the final target strain via the introduction of the CRE enzyme. It has a pMB1 origin of replication and thus can be maintained in any *E. coli* strain prior to being cut out and transferred along with the Zeocin® resistance cassette using SfiI restriction enzyme digestion and transfer into the pUT delivery vector thus generating a functional transposon. The sequence of the transposon is shown below (SEQ ID NO: 13):

```
5'GGCCGCCTAGGCCGCGGCCGCCTACTTCGTATAGCATACATTATACGA
AGTTATGTCTGACGCTCAGTGGAACGACGCGTAACTCACGTTAAGGGATT
TTGGTCATGATCAGCACGTTGACAATTAATCATCGGCATAGTATATCGGC
ATAGTATAATACGACAAGGTGAGGAACTAAAACATGGCCAAGTTGACCAG
TGCCGTTCCGGTGCTCACCGCGCGCGACGTCGCCGGAGCGGTCGAGTTCT
GGACCGACCGGCTCGGGTTCTCCCGGGACTTCGTGGAGGACGACTTCGCC
GGTGTGGTCCGGGACGACGTGACCCTGTTCATCAGCGCGGTCCAGGACCA
GGTGGTGCCGGACAACACCCTGGCCTGGGTGTGGGTGCGCGGCCTGGACG
AGCTGTACGCCGAGTGGTCGGAGGTCGTGTCCACGAACTTCCGGGACGCC
TCCGGGCCGGCCATGACCGAGATCGGCGAGCAGCCGTGGGGGCGGGAGTT
CGCCCTGCGCGACCCGGCCGGCAACTGCGTGCACTTCGTGGCCGAGGAGC
AGGACTGAATAACTTCGTATAGCATACATTATACGAAGTTATGGCCGCCT
AGGCC-3'.
```

The insertion of CspglB2 into this transposon and transfer into the pUT delivery vector resulted in plasmid pELLA2 and maintained in Transformax *E. coli* strain EC100D pir+ (Cambio U.K.).

Bacterial Conjugation

To enable transfer of the CspglB2 transposon cargo into the chromosome of a recipient *E. coli* strain or any other bacterium the plasmids pELLA2 was transferred into *E. coli* MFD a diaminopimelic acid (DAP) auxotroph. Growth medium was supplemented with Zeocin® 100 μg/ml and ampicillin 100 μg/ml. Both donor and recipient bacteria were growth until late exponential phase. Bacterial cells were pelleted by centrifugation, washed 3 times with PBS and mixed together in a ratio of 1:3 recipient to donor and spotted on a dry LB agar plate with no antibiotics for 4-8 hrs.

The cells were scraped and suspended in PBS and dilutions plated on LB agar with appropriate selection antibiotics to select for transconjugants. Individual colonies were picked up and screened for loss of the pUT backbone and for the presence of the transposon.

Generation of Unmarked pglB Insertion

The transposon carrying CspglB2 and loxP recombination sites around a Zeocin® resistance cassette was introduced into PoulVAc E. coli. Following selection for Zeocin® resistant colonies, the antibiotic selection marker was removed by introduction via electroporation, the temperature sensitive vector pCRE5 (Reference: Appl Environ Microbiol. 2008 February; 74(4): 1064-1075. Genetic Tools for Select-Agent-Compliant Manipulation of *Burkholderia pseudomallei*. Kyoung-Hee Choi, Takehiko Mima, Yveth Casart, Drew Rholl, Ayush Kumar, Ifor R. Beacham and Herbert P. Schweizer).

PoulVAc E. coli was cultured at 28° C. in the presence of kanamycin 50 µg/ml, rhamnose was added to induce expression at 0.2% final concentration and the organism subcultured several times to select for colonies that had lost resistance to Zeocin® but maintained resistance to kanamycin indicating that the bleomycin resistance gene had been flipped out of the chromosome.

This *E. coli* mutant was then sub-cultured at 42° C. to cure out the pCRE5 plasmid. Screening for colonies that had once again become sensitive to kanamycin confirmed loss of pCRE5 and completed generation of an unmarked inducible copy of pglB on the chromosome of *E. coli*.

Carrier Polypeptide

Attenuated bacterial strains are transformed with the plasmid pGVXN150:GT-ExoA encoding a modified carrier polypeptide [GT-ExoA]. The GT-ExoA construct was engineered to express a modified version of *P. aeruginosa* Exotoxin A in the vector pGH and closed into a vector derived from pEC415 using the restriction enzymes NheI and EcoRI (NEB). The synthesized protein contains two internal modifications that allow glycosylation of the protein by Pgl, as well as containing four N-glycosylation sequons at the N terminal and an additional 4 at the C terminals glycotags. In addition, a hexa-histidine tag was added to the C-terminus of the protein to facilitate putification and an and an *E. coli* DsbA signal peptide was added to the N-terminal sequences enabling Sec-dependent secretion to the periplasm. pGVXN150: GT-ExoA is ampicillin resistant and L-(+)-Arabinose inducible. The construct sequence was then confirmed using Sanger sequences with the primers GTExoA NF (SEQ ID NO 14; GCGCTGGCTGGTT-TAGTTT), GTExoA NR (SEQ ID NO 15; CGCAT-TCGTTCCAGAGGT), GTExoA CF (SEQ ID NO 16; GACAAGGAACAGGCGATCAG) and GTExoA CR (SEQ ID NO 17; TGGTGATGATGGTGATGGTC).

Reducing the toxicity of PglB

Protein glycan coupling technology requires the use of *Campylobacter jejuni* PglB. This enzyme has 13 transmembrane domain and is toxic when overexpressed in *E. coli*. The pglB gene was originally amplified by PCR with oligonucleotides PglBEcoRI (EcoRI in bold) using the primers (SEQ ID NO 37: AAGAATTCATGTT-GAAAAAAGAGTATTTAAAAAACCC) and PglBNcoI-HA (SEQ ID NO 38: AACCATGGTTAAGCGTAATCTGGAA-CATCGTATGGGTAAATTTTAAGTTTAAAAACCT-TAGC), using Pfu polymerase with pACYC(pgl) as template. Oligonucleotide PglBNcoI-HA encodes an HA-tag to follow PglB expression by Western blot. The PCR product was digested with EcoRI and NcoI and cloned in the same sites of vector pMLBAD. The plasmid obtained was named pMAF10. Arabinose-dependent expression of PglB was confirmed by Western blot (Feldman et al. 2005). This construct has been subcloned into the EcoRI site of the vector pEXT21 allowing for IPTG dependant inducible expression of CjpglB. This plasmid and ORF combination has been used for several years in order to produce several glycoconjugate vaccines. In a recent modification using PglB from *Campylobacter sputorum* we have carried out tests and found that the ribosome binding site is encoded within the pEXT21 vector itself. This means that translational efficiency is partly controlled by the distance between the RBS and the ATG start codon of pglB. We noticed that inserting the PglB coding gene into the vector pEXT21 with an extended 10 base pairs of DNA sequence resulted in reduced toxicity of the enzyme and subsequently increased growth in the carrier *E. coli* strain as measured by optical density. Therefore it may be possible to reduce the toxicity of *C. jejuni* PglB by the simple modification of insertion of additional nucleotides before the ATG start codon or alternatively clone the gene further away from the RBS carried within the expression plasmid.

Construction of pELLA3

The pglB gene from *C. sputorum* was amplified using the primers CsPglB1fwd: TTTT GAATTCGATTATCGC-CATGGCGTCAAATTTTAATTTCGCTAAA (SEQ ID NO 39) and the reverse primer CsPglB1rev: TTTT GAATTC TTATTTTTTGAGTTTATAAATTTTAGTTGAT (SEQ ID NO 40) using Accuprime Taq Hifi and the following cycling conditions 94° C./30 s, followed by 24 cycles of the following conditions 94° C./30 s, 53° C./30 s, 68° C./2 min. The PCR product was cut with the restriction enzyme EcoRI HF for 16 hr at 37° C. The plasmid pEXT21 was also cut with the restriction enzyme EcoRI HF for 16 hr at 37° C. Both plasmid and PCR product were purified with a PCR purification kit (QIAGEN UK) and the plasmid pEXT21 was dephosphorylated by treating with Antarctic phosphatase (NEB UK Ltd) at 37° C. for 1 hr. The enzyme was heat inactivated by heating at 80° C. for 2 min before the plasmid and the insert were ligated together using T4 DNA ligase (Promega UK) and the reaction was incubated overnight at 4° C. The ligation reaction was transformed into *E. coli* Dh10β cells (NEB UK Ltd) and recovered on LB Spectinomycin plates (80 µg/ml). Constructs were then sequenced to confirm that the cloned *C. sputorum* PglB had not gained any mutations during the cloning process. This new construct was named pELLA3.

In Vitro Mutagenesis of the *C. jejuni* 81116 pgl Locus Cloned in pACYC184

Mutagenesis of 11 genes in the *C. jejuni* 81116 glycosylation locus cloned in pACYC184 (pACYCpgl) was performed in vitro using a customised EZ::TNtransposon system (Epicentre, Madison, Wis., USA). Briefly, a kanamycin resistance cassette (Trieu-Cuot et al., 1985) lacking a transcriptional terminator and therefore unable to exert downstream polar effects was amplified by PCR and cloned into the multiple cloning site of the vector pMOD™<MCS> (Epicentre). This construct was linearized by ScaI digestion and the kanamycin resistance cassette along with flanking mosaic ends was amplified by PCR using primers FP-1 and RP-1 (Epicentre). The PCR product was combined with plasmid pACYCpgl (Wacker et al., 2002) in an in vitro transposition reaction performed according to manufacturer's instructions (Epicentre). The resultant pool of mutated pACYCpgl plasmids was electroporated into *E. coli* XL1-Blue MRF' (Stratagene) and putative mutants were screened by PCR to identify the location and orientation of the kanamycin cassette. We only used those mutants having the kanamycin resistance cassette inserted with the same transcriptional orientation as the genes of the glycosylation locus, which were also confirmed by sequence analysis.

EXAMPLE 1

The construct pELLA1 was transformed into *E. coli* CLM24 cells alongside a pEC415vector coding for *Pseudomonas aeruginosa* exotoxin A with a single internal glycosylation site and the plasmid pACYCpglB::km coding for the entire *C. jejuni* heptasaccharide with a disruption in the pglB gene by insertion of a miniTn5km2 element. As a comparison the exotoxin A and *C. jejuni* heptasaccharide coding constructs were transformed into an *E. coli* CLM24 cell carrying pEXT21pglB from *C. jejuni*. 500 ml LB containing 30 µg/ml$^{-1}$ cm, 100 µg/ml$^{-1}$ amp, 80 µg/ml$^{-1}$ spectinomycin were inoculated with 10 ml of an O/N culture of either CLM24 construct combination and incubated with shaking at 37° C. Optical density 600 nm reading were taken at hourly intervals and protein expression induced at an $OD_{600\ nm}$ of 0.4 by the addition of IPTG 1 mM and L-arabinose 0.2% final concentration. 5 hr post initial induction, 0.2% L-arabinose was added and $OD_{600\ nm}$ continued to be measured (FIG. 1A).

Figure 1B:
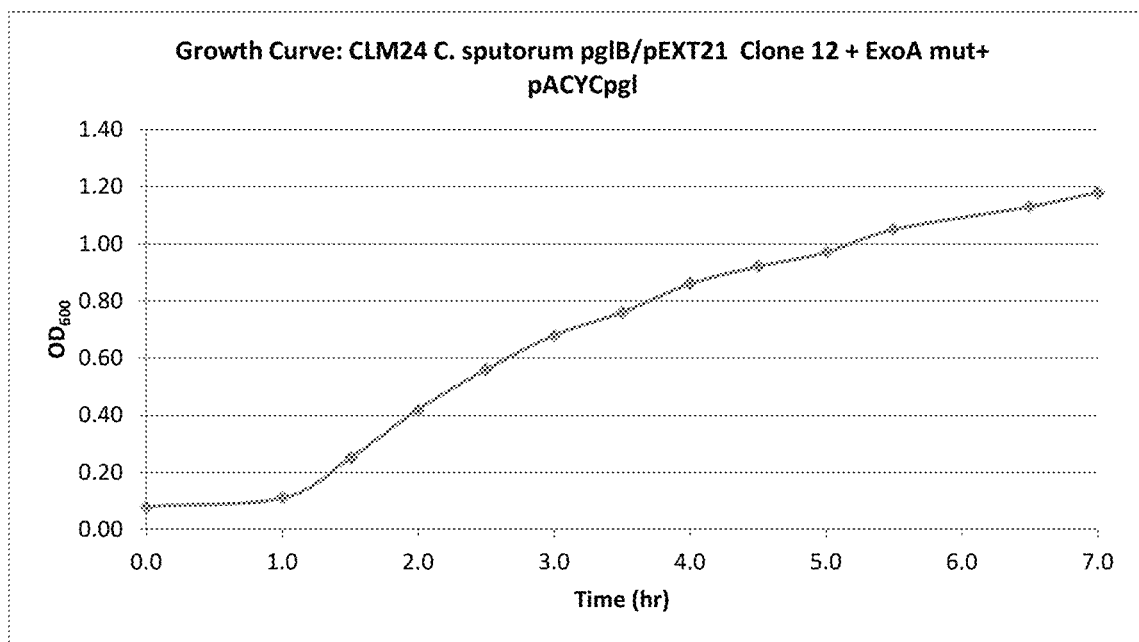

The growth of *E. coli* CLM24 cells without any induction of protein expression was also measured. This was carried out in the same way as described above for the *E. coli* CLM24 cells carrying pELLA1 except that no IPTG or L-arabinose was added (FIG. 1B).

EXAMPLE 2

Figure 2:
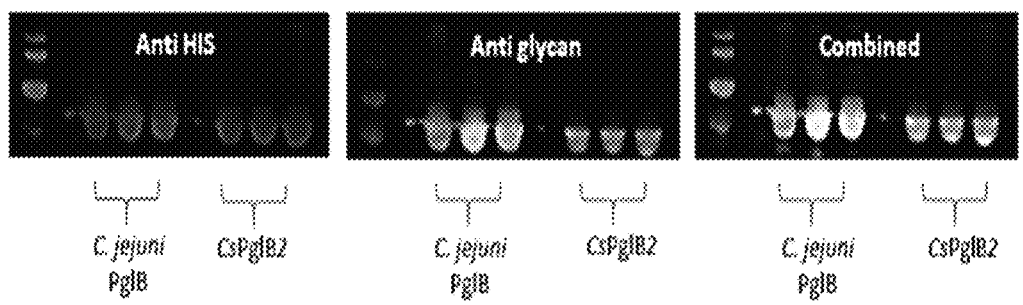
FIG. 2 illustrates glycosylation efficiency test in *E. coli* CLM24 glycosylating exotoxin A carrying a single glycosylation site (DQNRT (SEQ ID NO: 24) only).

*E. coli* CLM24 cultures carrying plasmids coding for singly glycosylatable exotoxinA, *C. sputorum* PglB2 or *C. jejuni* PglB were used to inoculate 500 ml of LB broth. Protein expression was induced as described in example 1 with the modification that the cultures were incubated for a further 16 hr after the second 0.2% L-arabinose addition. At this point cells were pelleted by centrifugation at 4000×g for 30 min and lysed using a high pressure cell homogeniser (Stansted Fluid power) HIS tagged exotoxinA was purified from CLM24 cells using NiNTA binding. Protein was separated on a 12% Bis-tris gel (Invitrogen) before transferring onto a nitrocellulose membrane. This was probed with primary rabbit hr6 anti-campy glycan antibody and mouse anti-HIS. Goat anti-rabbit and anti-mouse infrared dye labelled secondary antibodies were used to enable visualisation of glycoprotein using an Odyssey LI-COR scanner (LI-COR Biosciences UK Ltd) (FIG. 2).

Figure 3:
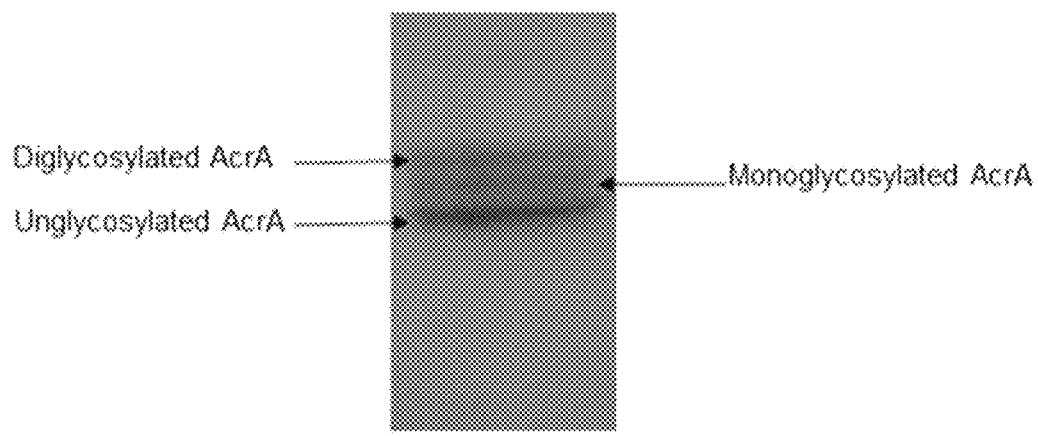
FIG. 3 illustrates how *C. sputorum* PglB is capable of generating a glycoprotein in the live attenuated strain Poul-Vac *E. coli*. The figure shows how AcrA protein mobility is affected glycosylation with *C. jejuni* heptasaccharide.
Figure 4:
FIG. 4 DNA sequence corresponding to constructs assembled. pEXT21 sequence (atttcacacaggaaaca); EcoRI restriction site (GAATTC); 10 nucleotide insertion (GATTATCGCC); *C. sputorum* pglB sequence (ATGGCGTCAAATTTTAATTTCGCTAAA). Contig indicates the construct assembled whilst expected is the expected *C. sputorum* pglB sequence.

EXAMPLE 3 pACYCpglB::kan was introduced into PoulVAC *E. coli* by electroporation alongside the plasmid pWA2 coding for a HIS tagged diglycosylatable CmeA and pELLA1. After induction with 1 mM IPTG and a total of 24 hr incubation at 37° C. with shaking. 200 ml of culture was obtained and centrifuged at 10,000×g for 10 min. Cells were lysed by high pressure and purification carried out using NiNTA. The protein was then purified according to manufacturer's instructions (QIAExpressioninst, Qiagen UK) and eluted in 4×0.5 ml before concentrating the sample to 50 µl. An equal volume of 2×SDS PAGE loading dye was added 20 µl was loaded into a 12% Bis-Tris gel and stained by coomassie (FIG. 3).

EXAMPLE 4

*Salmonella Typhimurium* strain SL3749 was transformed with pUA31 (coding for the acceptor protein CjaA), pACYCpglB::km (coding for *C. jejuni* heptasaccharide coding locus but with pglB knocked out) and pELLA1 (coding for IPTG inducible *C. jejuni* pglB). A 10 ml O/N 37° C. shaking culture was prepared and used to inoculate 200 ml of LB broth. This continue to be shaken 37° C. until an OD600 nm of 0.4 was reached. At this point 1 mM IPTG was added to induce CsPglB2 expression. The culture was incubated for a further 16 hr at 37° C. with shaking. Bacterial cultures were pelleted by centrifugation at 6000×g for 30 min and resuspended in 30 ml 25 mM Tris, 0.15 M NaCl pH 7.5 (TBS). Cells were lysed using a high-pressure cell homogeniser. 2% SDS and 1% Triton X-100 were added and the lysed material incubated for 3 hr at 4° C. with mixing. The material was then centrifuged at 4000×g for 20 min. Pellet was discarded before 300 µl of c-Myc sepharose (Thermo Scientific USA) was added. This was allowed to incubate O/N at 4° C. with mixing. The material was then centrifuged at 4000×g for 10 min and the supernatant removed. 1 ml TBS was added with 0.05% Tween. This was washed 5 times by pulsing at 10,000×g. Protein elution was achieved by the addition of 300 µl 2×SDS loading buffer containing 3 µl DTT and boiled for 10 minutes. Western blot was carried out to visualise the result.

EXAMPLE 5

We have used the transposon pELLA2 carrying an IPTG inducible copy of CspglB to integrate this gene into the chromosomes of glycoengineering *E. coli* strains W3110, CLM24, CLM37, SΘ874, SCM7, SCM6, SCM3 as well as PoulVAc *E. coli* and *S. typhimurium*.

The invention claimed is:

1. A vector comprising a transcription cassette comprising:
   i) a nucleic acid molecule comprising a nucleotide sequence set forth in SEQ ID NO: 1 or 2;
   ii) a nucleic acid molecule comprising a nucleotide sequence that is degenerate to the nucleotide sequence set forth in SEQ ID NO: 1 or 2 and encodes a polypeptide comprising an amino acid sequence as set forth in SEQ ID NO: 3;
   iii) a nucleic acid molecule comprising a nucleotide sequence that encodes an oligosaccharyltransferase polypeptide wherein said nucleotide sequence is at least 97% identical to the nucleotide sequence set forth in SEQ ID NO: 1; or
   iv) a nucleic acid molecule comprising a nucleotide sequence that encodes an oligosaccharyltransferase polypeptide wherein said nucleotide sequence is at least 77% identical to the nucleotide sequence set forth in SEQ ID NO: 2,
wherein said nucleic acid molecule is operably linked to a promoter adapted for expression in a bacterial host cell.

2. The vector according to claim 1 wherein said nucleic acid molecule comprises a nucleotide sequence that is 98% or 99% identical to the nucleotide sequence set forth in SEQ ID NO: 1.

3. The vector according to claim 1 wherein said nucleic acid molecule comprises a nucleotide sequence that is at least 78%, 79%, 80%, 81%, 82%, 83%, 84%, 85%, 86%, 87%, 88%, 89%, 90%, 91%, 92%, 93%, 94%, 95%, 96%, 97% identical to the nucleotide sequence set forth in SEQ ID NO: 2.

4. The vector according to claim 1 wherein said transcription cassette further comprises a nucleic acid molecule encoding a carrier polypeptide wherein said carrier polypeptide comprises one or more glycosylation motifs for said oligosaccharyltransferase.

5. The vector according to claim 1 wherein said oligosaccharyltransferase is operably linked to a regulatable promoter to provide regulated expression.

6. The vector according to claim 1 wherein said promoter is further operably linked to a ribosome binding site wherein there is provided a nucleotide spacer sequence between the 3' prime end of said ribosome binding site and the 5' initiating start codon of the nucleic acid molecule encoding said oligosaccharyltransferase wherein translation from the nucleic acid molecule encoding said oligosaccharyltransferase is reduced when compared to a control nucleic acid molecule encoding said recombinant polypeptide that does not comprise said nucleotide spacer sequence.

7. The vector according to claim 1, wherein said transcription cassette further comprises a nucleic acid molecule encoding a carrier polypeptide wherein said carrier polypeptide comprises one or more glycosylation motifs for said oligosaccharyltransferase and wherein said promoter is further operably linked to a ribosome binding site wherein there is provided a nucleotide spacer sequence between the 3' prime end of said ribosome binding site and the 5' initiating start codon of the nucleic acid molecule encoding said carrier polypeptide wherein translation from the nucleic acid molecule encoding said carrier polypeptide is reduced when compared to a control nucleic acid molecule encoding said recombinant polypeptide that does not comprise said nucleotide spacer sequence.

8. A bacterial cell genetically modified with the vector according to claim 1.

9. The bacterial cell according to claim 8 wherein said transcription cassette comprising said nucleic acid molecule encoding said oligosaccharyltransferase is stably integrated into the genome of said bacterial cell, and said bacterial cell further comprises a transcription cassette comprising a nucleic acid molecule encoding a carrier polypeptide, a polysaccharide biosynthetic locus, or both.

10. The bacterial cell according to claim 8 wherein said bacterial cell is a non-human pathogen.

11. The bacterial cell according to claim 8 wherein said bacterial cell is a zoonotic bacterial species.

12. A process for the production of one or more glycoconjugates comprising:
   i) providing a bacterial cell culture comprising a cell according to claim 8;
   ii) providing cell culture conditions; and optionally
   iii) isolating one or more glycoconjugates from the bacterial cell or cell culture medium.

13. A nucleic acid molecule encoding a polypeptide comprising at least 97% sequence identity to SEQ ID NO: 3, wherein SEQ ID NO: 3 is modified by deletion or substitution of at least one amino acid residue and said modified polypeptide has altered substrate specificity, increased oligosaccharyltransferase activity, or both, when compared to an unmodified oligosaccharyltransferase polypeptide comprising SEQ ID NO: 3.

14. The nucleic acid molecule according to claim 13 wherein said nucleic acid molecule comprises a nucleotide sequence that encodes a polypeptide comprising the amino acid sequence set forth in SEQ ID NO 43.

15. The nucleic acid molecule according to claim 14 wherein said isolated nucleic acid molecule comprising or consisting of the nucleotide sequence as set forth in SEQ ID NO: 42 or a degenerate variant thereof.

16. The nucleic acid molecule according to claim 15 wherein said nucleic acid molecule comprises or consists of the nucleotide sequence set forth in SEQ ID NO: 42.

17. The nucleic acid molecule according to claim 15 wherein said nucleic acid molecule is part of a transcription cassette.

18. A vector comprising a nucleic acid molecule according to claim 13 or a transcription cassette comprising the nucleic acid molecule.

19. A cell transformed or transfected with a nucleic acid molecule according to claim 13 or an expression vector comprising the nucleic acid molecule.

20. The cell according to claim 19 wherein said cell is a microbial cell.

21. A vector comprising a transcription cassette, comprising:
   i) a nucleic acid molecule comprising a nucleotide sequence set forth in SEQ ID NO: 1 or 2; or
   ii) a nucleic acid molecule comprising a nucleotide sequence that is degenerate to the nucleotide sequence set forth in SEQ ID NO: 1 or 2 and encodes a polypeptide comprising an amino acid sequence as set forth in SEQ ID NO: 3; wherein said nucleic acid molecule is operably linked to a promoter adapted for expression in a bacterial host cell.

22. The vector according to claim 1, wherein said vector is a plasmid.

23. The vector according to claim 1, wherein said vector is a transposon.

24. The vector according to claim 21, wherein said vector is a plasmid.

25. The vector according to claim 21, wherein said vector is a transposon.

26. The bacterial cell according to claim 8, wherein the nucleic acid molecule that encodes an oligosaccharyltransferase polypeptide is at least 98% identical to the nucleotide sequence set forth in SEQ ID NO: 1.

27. The bacterial cell according to claim 8, wherein the nucleic acid molecule that encodes an oligosaccharyltransferase polypeptide is at least 78% identical to the nucleotide sequence set forth in SEQ ID NO: 2.

\* \* \* \* \*

SEQUENCE LISTING

<160> NUMBER OF SEQ ID NOS: 49

<210> SEQ ID NO 1
<211> LENGTH: 2133
<212> TYPE: DNA
<213> ORGANISM: Campylobacter sputorum

<400> SEQUENCE: 1

| | | | | |
|---|---|---|---|---|
| atgtcaaatt | ttaatttcgc | taaatttcta | aataaattac ctagactttc | taaacatact | 60 |
| atattaatga | ttgttttagc | tgtttgtttt | gggatatttt gcagatttta | ctgggtagtt | 120 |
| tgggctagtg | cttatcccca | ttttatatgg | aatgatgaac ttatgataag | tacaaatgat | 180 |

```
ggatatgcat ttgctgaggg cacaagagat atgatagctg gttttcatca accaaacgat    240
ctttcttact atggctcatc tctttctaca cttagcatgt ggctatatag cattttgcca    300
ttttcattag aaactatact tttgtatatg agtacatttt tatctccact attagctgtg    360
cctttgatac ttataggtaa agaactaaac gcttcaaaag ctggatttat agctgcactt    420
ctagctgttg ttgcaaatag ttattataat agaacaatga gtggatatta tgatacagat    480
atgctaaata ttactcttcc tatgatggtt ttttggagca taacaagact tgttcaaaga    540
aaagagagag taaatttaat atttattcca gtttttatgg cgatatatgg atggtggtat    600
ccatcttctt actcactatt actcgcaatg attgggatgt ttgttttata taccattgtt    660
tttgaaagat atgaaaaact aaactatgaa gctatggttt ttatgatttt ggcaatcaca    720
agctttccta tacaaatcaa atttattata gttattattt tgtatgcttt gatctatttt    780
tatcaaagat tttttgataa aaaagtaata tttgcattaa ttatagcttc atcaatatgc    840
tttatatggc ttggcggatt aaatcctata ctttttaaca ttaaatttta tatatttaga    900
gacattgcag atagtggtga tactgttttt aaatttttca atgtaaatca aacaataaga    960
gaaagttccg cgatagattt taatacagtt gcaactagga ttagtgggca tttgatagta   1020
tttttggtat ctattgtagg atatatttta tttataaaaa acaataaaat tttactacta   1080
actttaccga ttctattttt aggtcttatg tcatttaaaa gtggtttaag atttacaata   1140
tactcagttc cagtaatggc ccttggtttt ggttattttg ttatgtattg ttttacaaag   1200
atagatataa aagatcgttt tttaggttat gcatttttat ttgttgtaac atttagtgca   1260
ttatatccat ctttaaaaca tatttatgat tataaggtat ttcctgtttt tacacatagc   1320
gaagttgaaa gtttggatga tttaaaaaat attgcaaaaa gagaagatta tgtgctttct   1380
tggtgggatt atggttatcc aataagatat tattctgatg taaaaactct catagatgga   1440
ggaaaacatc taggaagtga taacttcgca gttagctttg cacttggaag cgatcaaaac   1500
agctctgcaa atatggcaag attagaagtt gagtatacag aaagaaatta tgaggaaaaa   1560
tttggattaa atttaaaaca gattatgaaa gattataatg ctacaaatgt taatgagttt   1620
ttattatcat taaaagatgc aaatttagct ctgccaaagc aaacaagaga tatttattac   1680
tatttaccag atagaatgat atacatatat ccaacagtgc tagctttttc tagacttgat   1740
ttgacaacag ggcaagaatt tgctgagccg ttttttatag ttagtgagag attttcagct   1800
acaaatgata atcaaataat gttaaataat aatgttatat taagtagtga tggcactaaa   1860
ttatcaataa atggaaactc ttatagtgta aatacatatg tagaaacaag ttatgatcaa   1920
aatgaaaaat taaatgtaaa ttattttaac atagatccaa atagcaattt ttatgtgatt   1980
tttatgaaag attatttgag aattttggtt ttagataaaa ctttatatga tagtgcgtat   2040
attcaacttt ttgtattaga aaattatgat aaaaatttat ttgaaccagt gattttaaac   2100
ggatcaacta aaatttataa actcaaaaaa tga                                 2133
```

<210> SEQ ID NO 2
<211> LENGTH: 2133
<212> TYPE: DNA
<213> ORGANISM: Campylobacter sputorum

<400> SEQUENCE: 2

```
atgagtaatt ttaattttgc caaatttctg aacaagctgc ctagactaag caaacatacc     60
atcctgatga tcgtgctggc ggtgtgcttt ggcatctttt gtcgctttta ttgggttgtg    120
```

-continued

| | |
|---|---|
| tgggcgagtg cgtatccaca ttttatttgg aatgatgaac tgatgatctc tacaaatgat | 180 |
| ggctatgcgt ttgcggaagg tacacgcgat atgattgccg gctttcatca gccgaatgat | 240 |
| ctgtcatatt atggtagttc actgtccact ttaagcatgt ggctgtatag catcctgccg | 300 |
| ttttcattag aaaccatctt actgtatatg tcaacgtttc tgagtccact gctggcagtt | 360 |
| ccgttaatct taatcggtaa agaactgaat gcgtctaaag caggctttat tgcagccctg | 420 |
| ctggcagttg tggccaatag ctattataat cgcaccatgt caggctatta tgataccggat | 480 |
| atgctgaata tcaccttacc gatgatggtg ttttggagca tcacccgcct ggttcagcgc | 540 |
| aaagaacggg ttaatctcat ctttattcca gtgtttatgg ccatctatgg ttggtggtat | 600 |
| ccatcttcat attcactgct gctggccatg atcggcatgt tgtgctgta taccatcgtg | 660 |
| tttgaacgct atgaaaaact gaattatgaa gcaatggtgt ttatgattct ggcaatcact | 720 |
| agctttccga ttcagatcaa gtttatcatc gtgatcattc tgtatgcgtt aatctatttt | 780 |
| tatcagcgct ttttcgataa aaagttatc tttgccttaa tcattgcaag tagcatttgc | 840 |
| tttatttggt taggcggctt aaatccaatc ctgtttaata tcaaattta tatctttcgc | 900 |
| gacatagcgg attcaggcga tacggtgttt aaattcttca atgtgaatca gaccattcgc | 960 |
| gaaagtagcg ccatcgattt taatacagtt gcgacccgca tctcaggtca tctgattgtg | 1020 |
| tttctggtga gcatcgtggg ctatatcctg tttatcaaaa acaacaagat tttactgctg | 1080 |
| accttaccga tcctgtttct gggtctgatg tcgtttaaaa gcggcctgcg ctttacaatc | 1140 |
| tatagcgttc ctgtaatggc gttaggcttt ggctattttg tgatgtattg ctttacgaaa | 1200 |
| atcgacatca aagatcgctt tctgggctat gcctttctgt ttgtggtgac ctttagtgcc | 1260 |
| ctgtatccgt cactgaaaca tatctatgat acaaggtgt ttccagtgtt tacacatagc | 1320 |
| gaagtggaaa gcctggatga tctgaaaaat attgccaaac gcgaagatta tgtgctgtct | 1380 |
| tggtgggatt atggctatcc gattcgctat tatagcgatg ttaaaacact gatcgatggc | 1440 |
| ggtaaacatc taggttcaga taattttgcc gtgagctttg cactgggcag cgatcagaat | 1500 |
| agtagtgcaa atatggcccg cttagaagtg gaatatacgg aacgcaatta tgaagaaaaa | 1560 |
| tttggtctga atctgaaaca gatcatgaaa gattataatg caaccaatgt gaatgagttt | 1620 |
| ctgctgtctc tgaaagatgc caacctggcc ctgcctaaac agacacgcga tatatattat | 1680 |
| tatctgccgg atcgcatgat ctatatctat cctacagtgt tagcctttag tcgcctggat | 1740 |
| ctgacgacgg gccaggaatt tgcagaaccg ttttcatcg tgagcgaacg ctttagtgca | 1800 |
| accaatgata tcagatcat gttaaacaac aatgtgattc tttcatcaga tggaacaaaa | 1860 |
| ctgtcaatca atggcaatag ctattcagtt aatacttatg tagaaaccag ctacgatcag | 1920 |
| aacgaaaaac tgaatgttaa ttattttaat atcgatccga atagcaattt ttatgtgatc | 1980 |
| tttatgaaag attatctgcg catcttagtt ctggataaaa ccctgtatga tagcgcgtat | 2040 |
| atccagctgt ttgtgctgga aaattatgat aaaaatctgt ttgaaccagt catcctgaat | 2100 |
| ggtagtacga aaatctataa gctgaaaaaa taa | 2133 |

<210> SEQ ID NO 3
<211> LENGTH: 710
<212> TYPE: PRT
<213> ORGANISM: Campylobacter sputorum

<400> SEQUENCE: 3

Met Ser Asn Phe Asn Phe Ala Lys Phe Leu Asn Lys Leu Pro Arg Leu
1               5                   10                  15

```
Ser Lys His Thr Ile Leu Met Ile Val Leu Ala Val Cys Phe Gly Ile
             20                  25                  30

Phe Cys Arg Phe Tyr Trp Val Val Trp Ala Ser Ala Tyr Pro His Phe
         35                  40                  45

Ile Trp Asn Asp Glu Leu Met Ile Ser Thr Asn Asp Gly Tyr Ala Phe
     50                  55                  60

Ala Glu Gly Thr Arg Asp Met Ile Ala Gly Phe His Gln Pro Asn Asp
 65                  70                  75                  80

Leu Ser Tyr Tyr Gly Ser Ser Leu Ser Thr Leu Ser Met Trp Leu Tyr
                 85                  90                  95

Ser Ile Leu Pro Phe Ser Leu Gly Thr Ile Leu Leu Tyr Met Ser Thr
                100                 105                 110

Phe Leu Ser Pro Leu Leu Ala Val Pro Leu Ile Leu Ile Gly Lys Glu
            115                 120                 125

Leu Asn Ala Ser Lys Ala Gly Phe Ile Ala Ala Leu Leu Ala Val Val
        130                 135                 140

Ala Asn Ser Tyr Tyr Asn Arg Thr Met Ser Gly Tyr Tyr Asp Thr Asp
145                 150                 155                 160

Met Leu Asn Ile Thr Leu Pro Met Met Val Phe Trp Ser Ile Thr Arg
                165                 170                 175

Leu Val Gln Arg Lys Glu Arg Val Asn Leu Ile Phe Ile Pro Val Phe
                180                 185                 190

Met Ala Ile Tyr Gly Trp Trp Tyr Pro Ser Ser Tyr Ser Leu Leu Leu
            195                 200                 205

Ala Met Ile Gly Met Phe Val Leu Tyr Thr Ile Val Phe Glu Arg Tyr
        210                 215                 220

Glu Lys Leu Asn Tyr Glu Ala Met Val Phe Met Ile Leu Ala Ile Thr
225                 230                 235                 240

Ser Phe Pro Ile Gln Ile Lys Phe Ile Ile Val Ile Leu Tyr Ala
                245                 250                 255

Leu Ile Tyr Phe Tyr Gln Arg Phe Phe Asp Lys Lys Val Ile Phe Ala
            260                 265                 270

Leu Ile Ile Ala Ser Ser Ile Cys Phe Ile Trp Leu Gly Gly Leu Asn
        275                 280                 285

Pro Ile Leu Phe Asn Ile Lys Phe Tyr Ile Phe Arg Asp Ile Ala Asp
    290                 295                 300

Ser Gly Asp Thr Val Phe Lys Phe Phe Asn Val Asn Gln Thr Ile Arg
305                 310                 315                 320

Glu Ser Ser Ala Ile Asp Phe Asn Thr Val Ala Thr Arg Ile Ser Gly
                325                 330                 335

His Leu Ile Val Phe Leu Val Ser Ile Val Gly Tyr Ile Leu Phe Ile
            340                 345                 350

Lys Asn Asn Lys Ile Leu Leu Leu Thr Leu Pro Ile Leu Phe Leu Gly
        355                 360                 365

Leu Met Ser Phe Lys Ser Gly Leu Arg Phe Thr Ile Tyr Ser Val Pro
    370                 375                 380

Val Met Ala Leu Gly Phe Gly Tyr Phe Val Met Tyr Cys Phe Thr Lys
385                 390                 395                 400

Ile Asp Ile Lys Asp Arg Phe Leu Gly Tyr Ala Phe Leu Phe Val Val
                405                 410                 415

Thr Phe Ser Ala Leu Tyr Pro Ser Leu Lys His Ile Tyr Asp Tyr Lys
            420                 425                 430

Val Phe Pro Val Phe Thr His Ser Glu Val Glu Ser Leu Asp Asp Leu
```

```
                435                 440                 445
Lys Asn Ile Ala Lys Arg Glu Asp Tyr Val Leu Ser Trp Trp Asp Tyr
450                 455                 460

Gly Tyr Pro Ile Arg Tyr Tyr Ser Asp Val Lys Thr Leu Ile Asp Gly
465                 470                 475                 480

Gly Lys His Leu Gly Ser Asp Asn Phe Ala Val Ser Phe Ala Leu Gly
                485                 490                 495

Ser Asp Gln Asn Ser Ser Ala Asn Met Ala Arg Leu Glu Val Glu Tyr
            500                 505                 510

Thr Glu Arg Asn Tyr Glu Glu Lys Phe Gly Leu Asn Leu Lys Gln Ile
        515                 520                 525

Met Lys Asp Tyr Asn Ala Thr Asn Val Asn Glu Phe Leu Leu Ser Leu
    530                 535                 540

Lys Asp Ala Asn Leu Ala Leu Pro Lys Gln Thr Arg Asp Ile Tyr Tyr
545                 550                 555                 560

Tyr Leu Pro Asp Arg Met Ile Tyr Ile Tyr Pro Thr Val Leu Ala Phe
                565                 570                 575

Ser Arg Leu Asp Leu Thr Thr Gly Gln Glu Phe Ala Glu Pro Phe Phe
            580                 585                 590

Ile Val Ser Glu Arg Phe Ser Ala Thr Asn Asp Asn Gln Ile Met Leu
        595                 600                 605

Asn Asn Asn Val Ile Leu Ser Ser Asp Gly Thr Lys Leu Ser Ile Asn
    610                 615                 620

Gly Asn Ser Tyr Ser Val Asn Thr Tyr Val Glu Thr Ser Tyr Asp Gln
625                 630                 635                 640

Asn Glu Lys Leu Asn Val Asn Tyr Phe Asn Ile Asp Pro Asn Ser Asn
                645                 650                 655

Phe Tyr Val Ile Phe Met Lys Asp Tyr Leu Arg Ile Leu Val Leu Asp
            660                 665                 670

Lys Thr Leu Tyr Asp Ser Ala Tyr Ile Gln Leu Phe Val Leu Glu Asn
        675                 680                 685

Tyr Asp Lys Asn Leu Phe Glu Pro Val Ile Leu Asn Gly Ser Thr Lys
    690                 695                 700

Ile Tyr Lys Leu Lys Lys
705                 710

<210> SEQ ID NO 4
<211> LENGTH: 840
<212> TYPE: DNA
<213> ORGANISM: Pseudomonas aeruginosa

<400> SEQUENCE: 4
atgaaaaaaa tacttctaag tgttttaacg gcctttgttg cagtagtatt ggctgcttgt      60
ggaggaaatt ctgactctaa aactttaaat tctcttgata agatcaagca aaatggagtt     120
gttaggattg ggtatttggc gataaaacca ccttttggtt atgtggatga aaaggaaac      180 aatcaaggct atgatatagc tttagctaaa cgcatagcaa agaactttt tggcgatgaa      240 aataaggtgc aatttgttct tgttgaagct gcaataggg ttgagttttt aaaatcaaat      300
aaagtagata ttattttggc taattttact caaactccgc aaagggcaga gcaggttgat     360
ttttgctcgc cttatatgaa ggtagcttta ggcgtagctg taccaaagga tagtaatata     420
actagcgtag aagattaaa agataaaacc ttgcttttaa acaaaggcac aacagcagat     480
gcttatttta cgcaaaatta tcctaatatt aaaactttaa aatatgatca aaataccgaa     540
```

```
acctttgccg ctttgatgga taaaagaggc gatgctttaa gtcatgataa taccttactt    600
tttgcttggg tgaaagatca tcctgatttt aaaatgggta ttaaagagtt aggtaacaaa    660
gatgttatcg caccagcggt taaaaaggc gataaagaac ttaaagaatt tatcgataat     720
ttgatcatca aactaggcca agagcagttt tttcacaagg cttatgatga aactttaaaa    780
gctcattttg gagatgatgt taaggccgat gatgtagtga ttgaaggtgg aaaaatttaa    840
```

<210> SEQ ID NO 5
<211> LENGTH: 279
<212> TYPE: PRT
<213> ORGANISM: Pseudomonas aeruginosa

<400> SEQUENCE: 5

```
Met Lys Lys Ile Leu Leu Ser Val Leu Thr Ala Phe Val Ala Val Val
1               5                   10                  15

Leu Ala Ala Cys Gly Gly Asn Ser Asp Ser Lys Thr Leu Asn Ser Leu
                20                  25                  30

Asp Lys Ile Lys Gln Asn Gly Val Val Arg Ile Gly Val Phe Gly Asp
            35                  40                  45

Lys Pro Pro Phe Gly Tyr Val Asp Glu Lys Gly Asn Asn Gln Gly Tyr
        50                  55                  60

Asp Ile Ala Leu Ala Lys Arg Ile Ala Lys Glu Leu Phe Gly Asp Glu
65                  70                  75                  80

Asn Lys Val Gln Phe Val Leu Val Glu Ala Ala Asn Arg Val Glu Phe
                85                  90                  95

Leu Lys Ser Asn Lys Val Asp Ile Ile Leu Ala Asn Phe Thr Gln Thr
                100                 105                 110

Pro Gln Arg Ala Glu Gln Val Asp Phe Cys Ser Pro Tyr Met Lys Val
            115                 120                 125

Ala Leu Gly Val Ala Val Pro Lys Asp Ser Asn Ile Thr Ser Val Glu
        130                 135                 140

Asp Leu Lys Asp Lys Thr Leu Leu Leu Asn Lys Gly Thr Thr Ala Asp
145                 150                 155                 160

Ala Tyr Phe Thr Gln Asn Tyr Pro Asn Ile Lys Thr Leu Lys Tyr Asp
                165                 170                 175

Gln Asn Thr Glu Thr Phe Ala Ala Leu Met Asp Lys Arg Gly Asp Ala
            180                 185                 190

Leu Ser His Asp Asn Thr Leu Leu Phe Ala Trp Val Lys Asp His Pro
        195                 200                 205

Asp Phe Lys Met Gly Ile Lys Glu Leu Gly Asn Lys Asp Val Ile Ala
    210                 215                 220

Pro Ala Val Lys Lys Gly Asp Lys Glu Leu Lys Glu Phe Ile Asp Asn
225                 230                 235                 240

Leu Ile Ile Lys Leu Gly Gln Glu Gln Phe Phe His Lys Ala Tyr Asp
                245                 250                 255

Glu Thr Leu Lys Ala His Phe Gly Asp Asp Val Lys Ala Asp Asp Val
            260                 265                 270

Val Ile Glu Gly Gly Lys Ile
        275
```

<210> SEQ ID NO 6
<211> LENGTH: 1104
<212> TYPE: DNA
<213> ORGANISM: Campylobacter jejuni

<400> SEQUENCE: 6

```
atgaaattat tcaaaaaaa tactatttta gctttaggtg ttgtgctttt actcactgct    60
tgcagcaaag aagaagcacc aaaaatacaa atgccgcctc aacctgtaac aaccatgagt   120
gctaaatctg aagatttacc acttagtttt acttaccctg ctaaacttgt cagtgattat   180
gatgtcatta taaagcctca agttagtggc gtaatagaaa ataaacttTt taaagctgga   240
gataaagtaa aaaaggaca acattatttT attatagaac aagacaaatt taaagctagt   300
gttgattcgg cttacggaca agctttgatg gctaaggcaa ctttcgaaaa tgcaagcaag   360
gattttaatc gttctaaagc tcttTttagt aaaagtgcaa tctctcaaaa ggaatacgac   420
tcttctcttg ctacatttaa caattcaaaa gctagtctag caagtgctag agcacagctt   480
gcaaatgcaa gaattgatct agatcatacc gaaataaaag ctccttttga tggtactata   540
ggagatgctt tagttaatat aggagattat gtaagtgctt caacaactga actagttaga   600
gttacaaatt taaatcctat ttacgcagat ttctttattt cagatacaga taaactaaat   660
ttagtccgca atactcaaaa tggaaaatgg gatttagaca gcattcatgc aaatttaaat   720
cttaatggag aaaccgttca aggcaaactt tatttTattg attctgttat agatgctaat   780
agtggaacag taaagccaa agctatatt gacaacaaca actcaacact tttaccaggt   840
gcttttgcaa caattacttc agaaggtttt atacaaaaaa atggctttaa agtgcctcaa   900
atagctgtta acaaaatca aatgatgtt tatgttcttc ttgttaaaaa tggaaaagta   960
gaaaaatctt ctgtacatat aagctaccaa aacaatgaat atgccattat tgacaaagga  1020
ttacaaaatg gcgataaaat cattttagat aactttaaaa aaattcaagt tggtagcgaa  1080
gttaaagaaa ttggagcaca ataa                                        1104
```

<210> SEQ ID NO 7
<211> LENGTH: 367
<212> TYPE: PRT
<213> ORGANISM: Campylobacter jejuni

<400> SEQUENCE: 7

```
Met Lys Leu Phe Gln Lys Asn Thr Ile Leu Ala Leu Gly Val Val Leu
1               5                   10                  15

Leu Leu Thr Ala Cys Ser Lys Glu Glu Ala Pro Lys Ile Gln Met Pro
                20                  25                  30

Pro Gln Pro Val Thr Thr Met Ser Ala Lys Ser Glu Asp Leu Pro Leu
            35                  40                  45

Ser Phe Thr Tyr Pro Ala Lys Leu Val Ser Asp Tyr Asp Val Ile Ile
        50                  55                  60

Lys Pro Gln Val Ser Gly Val Ile Glu Asn Lys Leu Phe Lys Ala Gly
65                  70                  75                  80

Asp Lys Val Lys Lys Gly Gln Thr Leu Phe Ile Ile Glu Gln Asp Lys
                85                  90                  95

Phe Lys Ala Ser Val Asp Ser Ala Tyr Gly Gln Ala Leu Met Ala Lys
            100                 105                 110

Ala Thr Phe Glu Asn Ala Ser Lys Asp Phe Asn Arg Ser Lys Ala Leu
        115                 120                 125

Phe Ser Lys Ser Ala Ile Ser Gln Lys Glu Tyr Asp Ser Ser Leu Ala
    130                 135                 140

Thr Phe Asn Asn Ser Lys Ala Ser Leu Ala Ser Ala Arg Ala Gln Leu
145                 150                 155                 160

Ala Asn Ala Arg Ile Asp Leu Asp His Thr Glu Ile Lys Ala Pro Phe
                165                 170                 175
```

Asp Gly Thr Ile Gly Asp Ala Leu Val Asn Ile Gly Asp Tyr Val Ser
            180                 185                 190

Ala Ser Thr Thr Glu Leu Val Arg Val Thr Asn Leu Asn Pro Ile Tyr
            195                 200                 205

Ala Asp Phe Phe Ile Ser Asp Thr Asp Lys Leu Asn Leu Val Arg Asn
            210                 215                 220

Thr Gln Asn Gly Lys Trp Asp Leu Asp Ser Ile His Ala Asn Leu Asn
225                 230                 235                 240

Leu Asn Gly Glu Thr Val Gln Gly Lys Leu Tyr Phe Ile Asp Ser Val
            245                 250                 255

Ile Asp Ala Asn Ser Gly Thr Val Lys Ala Lys Ala Ile Phe Asp Asn
            260                 265                 270

Asn Asn Ser Thr Leu Leu Pro Gly Ala Phe Ala Thr Ile Thr Ser Glu
            275                 280                 285

Gly Phe Ile Gln Lys Asn Gly Phe Lys Val Pro Gln Ile Ala Val Lys
            290                 295                 300

Gln Asn Gln Asn Asp Val Tyr Val Leu Leu Val Lys Asn Gly Lys Val
305                 310                 315                 320

Glu Lys Ser Ser Val His Ile Ser Tyr Gln Asn Asn Glu Tyr Ala Ile
            325                 330                 335

Ile Asp Lys Gly Leu Gln Asn Gly Asp Lys Ile Ile Leu Asp Asn Phe
            340                 345                 350

Lys Lys Ile Gln Val Gly Ser Glu Val Lys Glu Ile Gly Ala Gln
            355                 360                 365

<210> SEQ ID NO 8
<211> LENGTH: 2112
<212> TYPE: DNA
<213> ORGANISM: Pseudomonas aeruginosa

<400> SEQUENCE: 8

| | |
|---|---|
| atgaaaaaga tttggctggc gctggctggt ttagttttag cgtttagcgc tagcgatcag | 60 |
| aacgcgaccg gcggtgacca aaatgccaca ggtggcgatc aaaacgccac cggcggtgac | 120 |
| cagaatgcga cagccgccga ggaagccttc gacctctgga cgaatgcgc caaggcctgc | 180 |
| gtgctcgacc tcaaggacgg cgtgcgttcc agccgcatga cgtcgaccc ggccatcgcc | 240 |
| gacaccaacg ccagggcgt gctgcactac tccatggtcc tggagggcgg caacgacgcg | 300 |
| ctcaagctgg ccatcgacaa cgccctcagc atcaccagcg acggcctgac catccgcctc | 360 |
| gaaggcggcg tcgagccgaa caagccggtg cgctacagct acacgcgcca ggcgcgcggc | 420 |
| agttggtcgc tgaactggct ggtaccgatc ggccacgaga agccctcgaa catcaaggtg | 480 |
| ttcatccacg aactgaacgc cggtaaccag ctcagccaca tgtcgccgat ctacaccatc | 540 |
| gagatgggcg acgagttgct ggcgaagctg gcgcgcgatg ccaccttctt cgtcagggcg | 600 |
| cacgagagca cgagatgca gccgacgctc gccatcagcc atgccgggt cagcgtggtc | 660 |
| atggctcagg cccagccgcg ccgggaaaag cgctggagcg aatgggccag cggcaaggtg | 720 |
| ttgtgcctgc tcgacccgct ggacggggtc tacaactacc tcgcccagca gcgctgcaac | 780 |
| ctcgacgata cctgggaagg caagatctac cgggtgctcg ccggcaaccc ggcgaagcat | 840 |
| gacctggaca tcaaggataa taataattct actcccacgg tcatcagtca tcgcctgcat | 900 |
| ttccccgagg gcgcagcct ggccgcgctg accgcgcacc aggcctgcca cctgccgctg | 960 |
| gaggccttca ctcgtcatcg ccagccgcgc ggctgggaac aactggagca gtgcggctat | 1020 |

-continued

```
ccggtgcagc ggctggtcgc cctctacctg gcggcgcgac tgtcgtggaa ccaggtcgac        1080
caggtgatcc gcaacgccct ggccagcccc ggcagcggcg cgacctgggc gaagcgatc         1140 cgcgagcagc cggagcaggc ccgtctggcc ctgaccctgg ccgccgccga gagcgagcgc        1200
ttcgtccggc agggcaccgg caacgacgag gccggcgcgg ccagcgccga cgtggtgagc        1260
ctgacctgcc ccgtcgccaa agatcaaaat agaactaaag gggaatgcgc gggcccggcg        1320
gacagcggcg acgccctgct ggagcgcaac tatcccactg gcgcggagtt cctcggcgac        1380
ggcggcgacg tcagcttcag caccgcggc  acgcagaact ggacggtgga gcggctgctc        1440
caggcgcacc gccaactgga ggagcgcggc tatgtgttcg tcggctacca cggcaccttc        1500
ctcgaagcgg cgcaaagcat cgtcttcggc ggggtgcgcg cgcgcagcca ggacctcgac        1560
gcgatctggc gcggttttcta tatcgccggc gatccggcgc tggcctacgg ctacgcccag       1620
gaccaggaac ccgacgcgcg cggccggatc cgcaacggtg ccctgctgcg ggtctatgtg        1680
ccgcgctgga gtctgccggg cttctaccgc accggcctga ccctggccgc gccggaggcg        1740
gcgggcgagg tcgaacggct gatcggccat ccgctgccgc tgcgcctgga cgccatcacc        1800
ggccccgagg aggaaggcgg gcgcgtgacc attctcggct ggccgctggc cgagcgcacc        1860
gtggtgattc cctcggcgat ccccaccgac ccgcgcaacg tcgcggcgga cctcgacccg        1920
tccagcatcc ccgacaagga acaggcgatc agcgccctgc cggactacgc cagccagccc        1980
ggcaaaccgc cgcgcgagga cttgaaggat cagaacgcga ccggcggtga ccaaaatgcc        2040
acaggtggcg atcaaaacgc caccggcggt gaccagaatg cgacagtcga ccatcaccat       2100
catcaccatt ga                                                            2112
```

<210> SEQ ID NO 9
<211> LENGTH: 697
<212> TYPE: PRT
<213> ORGANISM: Pseudomonas aeruginosa

<400> SEQUENCE: 9

```
Met Lys Lys Ile Trp Leu Ala Leu Ala Gly Leu Val Leu Ala Phe Ser
1               5                   10                  15

Ala Ser Asp Gln Asn Ala Thr Gly Gly Asp Gln Asn Ala Thr Gly Gly
            20                  25                  30

Asp Gln Asn Ala Thr Gly Gly Asp Gln Asn Ala Thr Ala Ala Glu Glu
        35                  40                  45

Ala Phe Asp Leu Trp Asn Glu Cys Ala Lys Ala Cys Val Leu Asp Leu
    50                  55                  60

Lys Asp Gly Val Arg Ser Ser Arg Met Ser Val Asp Pro Ala Ile Ala
65                  70                  75                  80

Asp Thr Asn Gly Gln Gly Val Leu His Tyr Ser Met Val Leu Glu Gly
                85                  90                  95

Gly Asn Asp Ala Leu Lys Leu Ala Ile Asp Asn Ala Leu Ser Ile Thr
            100                 105                 110

Ser Asp Gly Leu Thr Ile Arg Leu Glu Gly Gly Val Glu Pro Asn Lys
        115                 120                 125

Pro Val Arg Tyr Ser Tyr Thr Arg Gln Ala Arg Gly Ser Trp Ser Leu
    130                 135                 140

Asn Trp Leu Val Pro Ile Gly His Glu Lys Pro Ser Asn Ile Lys Val
145                 150                 155                 160

Phe Ile His Glu Leu Asn Ala Gly Asn Gln Leu Ser His Met Ser Pro
                165                 170                 175
```

```
Ile Tyr Thr Ile Glu Met Gly Asp Glu Leu Ala Lys Leu Ala Arg
            180                 185                 190

Asp Ala Thr Phe Phe Val Arg Ala His Glu Ser Asn Glu Met Gln Pro
        195                 200                 205

Thr Leu Ala Ile Ser His Ala Gly Val Ser Val Val Met Ala Gln Ala
        210                 215                 220

Gln Pro Arg Arg Glu Lys Arg Trp Ser Glu Trp Ala Ser Gly Lys Val
225                 230                 235                 240

Leu Cys Leu Leu Asp Pro Leu Asp Gly Val Tyr Asn Tyr Leu Ala Gln
                245                 250                 255

Gln Arg Cys Asn Leu Asp Asp Thr Trp Glu Gly Lys Ile Tyr Arg Val
            260                 265                 270

Leu Ala Gly Asn Pro Ala Lys His Asp Leu Asp Ile Lys Asp Asn Asn
        275                 280                 285

Asn Ser Thr Pro Thr Val Ile Ser His Arg Leu His Phe Pro Glu Gly
        290                 295                 300

Gly Ser Leu Ala Ala Leu Thr Ala His Gln Ala Cys His Leu Pro Leu
305                 310                 315                 320

Glu Ala Phe Thr Arg His Arg Gln Pro Arg Gly Trp Glu Gln Leu Glu
                325                 330                 335

Gln Cys Gly Tyr Pro Val Gln Arg Leu Val Ala Leu Tyr Leu Ala Ala
            340                 345                 350

Arg Leu Ser Trp Asn Gln Val Asp Gln Val Ile Arg Asn Ala Leu Ala
        355                 360                 365

Ser Pro Gly Ser Gly Asp Leu Gly Glu Ala Ile Arg Glu Gln Pro
370                 375                 380

Glu Gln Ala Arg Leu Ala Leu Thr Leu Ala Ala Glu Ser Glu Arg
385                 390                 395                 400

Phe Val Arg Gln Gly Thr Gly Asn Asp Glu Ala Gly Ala Ser Ala
                405                 410                 415

Asp Val Val Ser Leu Thr Cys Pro Val Ala Lys Asp Gln Asn Arg Thr
            420                 425                 430

Lys Gly Glu Cys Ala Gly Pro Ala Asp Ser Gly Asp Ala Leu Leu Glu
        435                 440                 445

Arg Asn Tyr Pro Thr Gly Ala Glu Phe Leu Gly Asp Gly Asp Val
        450                 455                 460

Ser Phe Ser Thr Arg Gly Thr Gln Asn Trp Thr Val Glu Arg Leu Leu
465                 470                 475                 480

Gln Ala His Arg Gln Leu Glu Glu Arg Gly Tyr Val Phe Val Gly Tyr
                485                 490                 495

His Gly Thr Phe Leu Glu Ala Ala Gln Ser Ile Val Phe Gly Gly Val
            500                 505                 510

Arg Ala Arg Ser Gln Asp Leu Asp Ala Ile Trp Arg Gly Phe Tyr Ile
        515                 520                 525

Ala Gly Asp Pro Ala Leu Ala Tyr Gly Tyr Ala Gln Asp Gln Glu Pro
        530                 535                 540

Asp Ala Arg Gly Arg Ile Arg Asn Gly Ala Leu Leu Arg Val Tyr Val
545                 550                 555                 560

Pro Arg Trp Ser Leu Pro Gly Phe Tyr Arg Thr Gly Leu Thr Leu Ala
                565                 570                 575

Ala Pro Glu Ala Ala Gly Glu Val Glu Arg Leu Ile Gly His Pro Leu
            580                 585                 590

Pro Leu Arg Leu Asp Ala Ile Thr Gly Pro Glu Glu Glu Gly Gly Arg
```

|  | 595 |  | 600 |  | 605 |  |  |  |
| --- | --- | --- | --- | --- | --- | --- | --- | --- |

Val Thr Ile Leu Gly Trp Pro Leu Ala Glu Arg Thr Val Val Ile Pro
 610                    615                   620

Ser Ala Ile Pro Thr Asp Pro Arg Asn Val Gly Gly Asp Leu Asp Pro
625                    630                   635                 640

Ser Ser Ile Pro Asp Lys Glu Gln Ala Ile Ser Ala Leu Pro Asp Tyr
                645                   650                   655

Ala Ser Gln Pro Gly Lys Pro Pro Arg Glu Asp Leu Lys Asp Gln Asn
                660                   665                   670

Ala Thr Gly Gly Asp Gln Asn Ala Thr Gly Gly Asp Gln Asn Ala Thr
            675                   680                   685

Gly Gly Asp Gln Asn Ala Thr Val Asp
690                   695

<210> SEQ ID NO 10
<211> LENGTH: 14645
<212> TYPE: DNA
<213> ORGANISM: Campylobacter jejuni

<400> SEQUENCE: 10

| atgaaaattc ttattagcgg tggtgcaggt tatataggtt ctcatacttt aagacaattt | 60 |
| --- | --- |
| ttaaaaacag atcatgaaat ttgtgtttta gataatcttt ctaagggttc taaaatcgca | 120 |
| atagaagatt tgcaaaaaac aagagctttt aaattttcg aacaagattt aagtgatttt | 180 |
| caaggcgtaa aagcattgtt tgagagagaa aaatttgacg ctattgtgca ttttgcagca | 240 |
| agcattgaag ttttgaaag tatgcaaaat cctttaaaat attatatgaa caacactgtt | 300 |
| aatacgacaa atctcatcga aacttgtttg caaactggag tgaataaatt tatattttct | 360 |
| tcaacggcgg ccacttatgg cgaaccacaa actcccgttg tgagcgaaac aagtccttta | 420 |
| gcacctatta atccttatgg gcgtagtaag cttatgagtg aagaagtttt gcgtgatgca | 480 |
| agtatggcaa atcctgaatt taagcattgt attttaagat attttaatgt tgcaggtgct | 540 |
| tgtatggatt atactttagg acaacgctat ccaaaagcga ctttgcttat aaaagttgca | 600 |
| gctgaatgtg ccgcaggaaa acgtgataaa cttttcatat ttggcgatga ttatgataca | 660 |
| aaagatggta cttgcataag agattttatc catgtagatg atatttcaag tgcacattta | 720 |
| gcggctttgg attattttaaa agagaatgaa agcaatgttt taatgtagg ttatggacat | 780 |
| ggttttagcg taaagaagt gattgaagcg atgaaaaaag ttagcggagt ggattttaaa | 840 |
| gtagaacttg ccccacgccg tgcgggtgat cctagtgtat tgattctga tgcaagtaaa | 900 |
| atcagaaatc ttacttcttg gcagcctaaa tatgatgatt tagagcttat tgtaaatct | 960 |
| gcttttgatt gggaaaaaca gtgttaaaaa aacttttttt tattttaagc aaggaagata | 1020 |
| aaaattttt attttcttg cttgttttt cagtatttgt ttctttata gaaacttttg | 1080 |
| cgatttcttt ggtaatgcct tttatcactt tggctagtga ttttcttat tttgatcgta | 1140 |
| ataaatattt aatcagccta aaagaatatc ttaatatccc tgttttgaa atcattgttt | 1200 |
| attttggagt ggggcttatt gttttttatg tatttagagc tttgttaaat gcgtattatt | 1260 |
| ttcatctttt ggcaagattt tctaaaggac gttatcatgc gatcgcttat aaggttttt | 1320 |
| ctaaattttt aaatattaat tatgaaaaat ttactcaaaa aaatcaatct gaaattttaa | 1380 |
| agtccattac agggggaagtt tataatctaa gcactatgat ttcatcattt ttactttga | 1440 |
| tgagtgaaat tttgtagtg cttttgcttt atgcttaat gctttgatt aattataaaa | 1500 |
| tcactttatt tttaagtatt tttatggtgt taaatgcttt tattttagtg aaaattttaa | 1560 |

```
gccctatcat taaaaaagca ggactaagac gcgaagaagc gatgaaaaat ttcttcgaaa    1620
ttttaaatac aaatttaaat aattttaaat ttatcaagct taaaaccaaa gaagatggag    1680
tattaagtct ttttaaagca caaagtgaag cttttcctaa agcaaatatt accaatgaaa    1740
gcgtagctgc ggtgcctaga atttatcttg aaggaatagg cttttgtgtg cttgttttta    1800
tcgtggtatt tttggttttg aaaaatgaaa gtgatatttc aggtatttta tccacgattt    1860
ctatttttgt tttagcgctt tatcgcttaa tgccaagcgc aaatcgtatt atcacaagtt    1920
atcatgattt gctttattat cattcttctt tgaatattat ttatcaaaat ttaagacaag    1980
aagaagaaaa tttgggcgag ggaaaattaa gttttaatca agagcttaaa atttgcaatc    2040
ttagctttgg ttatgaggga aaaaaatatt tatttaaaaa tcttaattta aacattaaaa    2100
aaggtgaaaa aatcgctttt ataggggaga gtggttgtgg aaaaagtacc ttagtagatc    2160
ttatcatagg acttttaaaa ccaaagaag ggcaaatttt aattgataag caagaattaa     2220
atgcaagtaa tgcaaaaaat tatcccgcaaa aaataggcta tatcccgcaa aatatctatc    2280
tttttaatga tagcatagct aaaaatatca cttttggaga tgcggttgat gaagaaaaac    2340
ttaataaggt tatcaaacaa gcaaatttag agcattttat aaaaaattta cctcaaggag    2400
ttcagacaaa agtaggcgat ggggggagta atttaagcgg gggacaaaaa caacgcatag    2460
ctatagcaag ggctttgtat ttagagcctg aaatttagt gcttgatgaa gcaacttctg     2520
cgcttgatac tcaaagtgaa gcaaaaatca tggatgaaat ttataaaatt tctaaagata    2580
aaaccatgat tattatcgca catcgccttt ctacgataac gcaatgtgat aaggtttatc    2640
gtttagaaca cggtaagctt aaagaggaga atgatgaaa ataagcttta ttatcgcaac     2700
tttaaattca ggaggcgctg agcgtgtttt agtaaccta gctaatgcgc tttgcaaaga     2760
gcatgaagta agtattatta aatttcatac aggagaatct ttttataagc ttgaaaatga    2820
agttaaagtt acaagtttag aacaatttag atttgacacg ctttatcata aaatcgcaag    2880
tcgttttaag aaatttttg ccttaagaaa ggctttaaaa gaaagtaagg ctgatgtttt     2940
tatttctttt ttggatacaa ctaatattgc ttgtattcta gctaatatag gacttaaaac    3000
tccactcatc attagcgagc atagtaatga agcgtattta aaacctaaaa cttggcgttt    3060
tttaagaagg gtaagctatc ctttttgtga tgctttaagt gtgcttggaa gcagtgataa    3120
ggtgtattat gaaagatttg taaaaagggt taagctttta ttaaaccctt gtcatttag    3180 cgatgaaatt ccttttgatt ctagttttga aaagaaaat ttggttcttt ttatagggcg     3240
tttagatcac aacaaaaacc ctgtaatgtt tttaaaagct atagcacatt tggataaaaa    3300
tttgcaagaa aattataaat ttgttatagc aggagatgga gagttaaggc aagaacttga    3360
atacaaggta aaatctttag gaataaaagt tgatttttta ggacgcgttg aaaatgtcaa    3420
ggctctttat gaaaaagcaa aagtgctttg cctttgttct tttgtagagg gtttgccaac    3480
ggttttaatt gaaagtttgt attttgaggt ttgtagaatt tcaagttctt attataatgg    3540
tgctaaggat ttaatcaaag ataatcatga tgggcttttg gtaggttgtg atgatgaaat    3600
agcacttgct aaaaaacttg aacttgtttt aaatgatgaa aattttagaa aagaacttgt    3660
aaataatgcc aaacaaggt gtaaagactt tgaaatttct aacatcaaag aagaatggct     3720
taagcttata gtcgaggtta aaatgcctaa aactttctgt tatagtgcca acttttaatc    3780
gtcaagtttt gttagaaaag gctattaaaa gcatacaaaa tcaagatttt aaagatttag    3840
aaatcattgt aagcgatgat aattctagtg atgatactaa agtgtggtg caaaatttac     3900
```

```
aaaaagatga tgatcgcatt aagtattttt taaatcaaaa ttacaaacaa ggcccaaatg    3960
gcaataaaaa caatggctta gatcaagcaa gtggcgagtt tgtaacttttt ttagatgatg    4020 atgatgagct tttatctggg gctttaagta ccttgatgca aaaagcaaat gagggttatg    4080
ctcatgtttt tggaaattgt ttgatagaaa aagaaggaaa tttaagcaag gaatttagcg    4140
gtaagggctt ggaaaaagat agtgaaattt ctaaaaaaga ttttttaatg gctaaattta    4200
gcggagagtt tttttctgtt tttaaaaaat ctctacttga aaacaagcgt tttaatgaag    4260
aattttatgg caatgaagcc acgctttggg taaatttata caaggaaaaa agttttata    4320 tccataaggc ttttaggatt tataggattt ttaggcaaga tagcgtgact ttaggggcga    4380
gtaaaaatgc tcatagggtg tatttgggat atttagagct tgctaaaatt ttagaaaatg    4440
aacttagaat gagtaaggat aaagattata aaaaaacttg tgcgagttat tataaaatgg    4500
cagcttatta tgcaaaactt gcaaaaaatt ataaagctct ttataagtgt tgtttaaaa    4560 gcctgagtat aaaaatcaac gctcctgctt tgatattact cattttaagt ataattccaa    4620
ataatatgat tgaaaaatta tcaaaaattc gggtggcttt atgcaaaaat taggcatttt    4680
tatttattct ttaggaagtg gtggtgctga agagttgtg gcgactttat tgcctatttt    4740
aagtttgaaa tttgaagtgc atttgatttt aatgaatgat aaaatttctt atgaaattcc    4800
agagtgtcaa attcatttt tagaatgttc aaaacctagt gaaaatccta ttttgaaatt    4860
tttaaaacta ccttttttgg cttaaaaata taaaaaactt tgcagaaatt taggcattga    4920
tacagaattt gtttttttaa atcgacctaa ttatatagcc ttaatggcaa gaatgtttgg    4980
aaacaaaact cgccttgtga tcaatgaatg cactacgcca agtgtgatgt atgcgaaaaa    5040 taatttaat tctttggcaa ataaattttt aatttctttg ctttacccaa aagctgattt    5100
aatcttgcct aattctaagg gaaatttaga agatttagtg caaaattta gtataaatcc    5160 aaaaaaatgt gaaatttttat acaatgccat cgatttagaa aatatagagc aaaaagctct    5220
tgaagatgta gctttaaaag ataaatttat tttaagtgta ggcaggcttg ataaaggtaa    5280
aaatcatgct ttattaattc gtgcttatgc aagattgaaa acagatttaa agcttgtgat    5340
tttaggtgaa ggtgtgctta agatgagct tttagctttg attaaagagt taaatttaga    5400
agaaaaggtt ttgcttttag gatttgataa taatccttat aaatacatgg ctaaatgcga    5460
attttttgct tttgcttctg tatttgaagg cttttcaaat gttttaattg aaagcttagc    5520
ttgttcttgt gcggtggttt gcactgatca taaaagtggc gcaagagagc ttttttggcga    5580 tgatgaattt ggacttttag tagaagtaga taatgaaaac tccatgtttc agggtttaaa    5640
gactatgctt gaagacgata aattaagaaa agcgtataaa aataaggcta aaactagggc    5700
taaagctttt gataaagtaa aaattgcacg cgatgctttg aaatatttat taggataaaa    5760
gatgttgaaa aaagagtatt taaaaaaccc ttatttagtt ttgtttgcga tgattatatt    5820
agcttatgtt tttagtgtat tttgcaggtt ttattgggtt tggtgggcaa gtgagtttaa    5880
tgagtatttt ttcaataatc agttaatgat catttcaaat gatggctatg cttttgctga    5940
gggcgcaaga gatatgatag caggttttca tcagcctaat gatttgagtt attatggatc    6000 ttcttatcc gcgcttactt attggcttta taaaatcaca ccttttttctt ttgaaagtat    6060 cattttatat atgagtactt ttttatcttc tttggtggtg attcctacta ttttgctagc    6120
taacgaatac aaaacgtcctt taatgggctt tgtagctgct cttttagcaa gtatagcaaa    6180
cagttattat aatcgcacta tgagtgggta ttatgatacg gatatgctgg taattgtttt    6240
gcctatgttt atttttatttt ttatggtaag aatgattttta aaaaaagact ttttttcatt    6300
```

```
gattgccttg ccgttatttta taggaattta tctttggtgg tatccttcaa gttatacttt    6360
aaatgtagct ttaattggac ttttttttaat ttatacactt attttttcata gaaaagaaaa    6420 gatttttttat atagctgtga ttttgtcttc tcttactctt tcaaatatag catggtttta    6480
tcaaagtgcc attatagtaa tacttttttgc tttattcgcc ttagagcaaa aacgcttaaa    6540
ttttatgatt ataggaattt taggtagtgc aactttgata ttttttgattt taagtggtgg    6600 ggttgatcct atactttatc agcttaaatt ttatatttttt agaagtgatg aaagtgcgaa    6660
tttaacgcag ggctttatgt attttaatgt caatcaaacc atacaagaag ttgaaaatgt    6720
agatcttagc gaatttatgc gaagaattag tggtagtgaa attgttttttt tgtttctttt    6780 gtttggttttt gtatggcttt tgagaaaaca taaaagtatg attatggctt tacctatatt    6840
ggtgcttggg ttttttagcct taaaggggggg gcttagattt accatttatt ctgtacctgt    6900
aatggcctta ggatttggtt tttattgag cgagtttaag gctataatgg ttaaaaaata    6960
tagccaatta acttcaaatg tttgtattgt ttttgcaact attttgactt tagctccagt    7020
atttatccat atttacaact ataaagcgcc aacagtttttt tctcaaaatg aagcatcatt    7080
attaaatcaa ttaaaaaata tagccaatag agaagattat gtggtaactt ggtgggatta    7140
tggttatcct gtgcgttatt atagcgatgt gaaaacttta gtagatggtg aaagcatttt    7200
aggtaaggat aattttttttcc cttctttttgc tttaagcaaa gatgaacaag ctgcagctaa    7260
tatggcaaga cttagtgtag aatatacaga aaaaagcttt tatgctccgc aaaatgatat    7320
tttaaaaaca gacatttttgc aagccatgat gaaagattat aatcaaagca atgtggattt    7380
gtttctagct tcattatcaa aacctgatttt taaaatcgat acgccaaaaa ctcgtgatat    7440
ttatctttat atgcccgcta gaatgtctttt gatttttttct acggtggcta gttttttcttt    7500 tattaatttta gatacaggag ttttggataa ccctttttacc tttagcacag cttatccact    7560
tgatgttaaa aatggagaaa tttatcttag caacggagtg gtttttaagcg atgattttag    7620 aagtttttaaa ataggtgata atgtggtttc tgtaaatagt atcgtagaga ttaattctat    7680
taaacaaggt gaatacaaaa tcactccaat tgatgataag gctcagtttt atatttttta    7740
tttaaaggat agtgctattc cttacgcaca atttatttttta atggataaaa ccatgtttaa    7800
tagtgcttat gtgcaaatgt ttttttttttagg aaattatgat aagaatttat ttgacttggt    7860
gattaattct agagatgcta aggttttttaa acttaaaatt taagggttga aaatgagaat    7920
aggattttta tcacatgcag gagcaagtat ttatcatttt agaatgccta ttataaaagc    7980
attaaaagat agaaaagatg aagttttttgt tatagtgccg caagatgaat acacgcaaaa    8040
acttagagat cttggtttaa aagtaattgt ttatgagttt tcaagagcta gtttaaatcc    8100
ttttgtagtt ttaagaatt ttttttatct tgctaaggtt ttaaaaaatt taaatcttga    8160
tcttattcaa agtgcggcac acaaaagcaa taccttttgga atttttagcgg caaaatgggc    8220 aaaaattcct tatcgttttttg ctttggtaga aggcttggga tcttttttata tagatcaagg    8280 ttttaaggca aatttagtac gttttgttat taataatctt tataaattaa gttttaaatt    8340
tgcacaccaa tttatttttttg tcaatgaaag taatgccgag tttatgcgga atttaggact    8400
taaggaaaat aaaatttgtg tgataaaatc cgtagggatc aatttaaaaa aatttttttcc    8460 tattttatata gaatcggaaa aaaaagagct ttttttggaga aatttaaata tagataaaaa    8520
acctattgtt cttatgatag caagagcttt atggcataaa ggtgtaaaag aatttttatga    8580 aagtgctact atgctaaaag acaaagcaaa ttttgtttta gttggtggaa gagatgaaaa    8640
```

```
tccttcttgt gcgagtttgg agttttaaa ctcgggtgtg gtgcattatt tgggtgctag    8700
aagtgatata gtcgagcttt tgcaaaattg tgatattttt gttttaccaa gctataaaga    8760
aggctttcct gtaagtgttt tggaggcaaa agcttgtggc aaggctatag tggtgagtga    8820
ttgtgaaggt tgtgtagagg ctatttctaa tgcttatgat ggactttggg caaaaacaaa    8880
aaatgctaag gatttaagcg aaaaaatttc acttttatta gaagatgaaa aattaagatt    8940
aaatttagct aaaaatgctg cccaagatgc tttacaatac gatgaaaata atatcgcaca    9000
gcgttattta aaactttatg ataggtaat taagaatgta tgaaaaagtt tttaaaagaa    9060
tttttgattt tatttagct ttagtgcttt tagtactttt ttctccggtg attttaatca    9120
ctgctttact tttaaaaatc actcaaggaa gtgtgatttt cactcaaaat cgccctgggt    9180
tagatgaaaa aattttaaa atttataaat ttaaaaccat gagcgatgaa agagatgaga    9240
agggtgagtt attaagcgat gaattgcgtt tgaaagcctt tggaaaaatt gttagaagct    9300
taagtttgga tgagcttttg caacttttta atgtttaaa aggggatatg agttttgtgg    9360
ggcctagacc tcttttggtt gagtatttat ccctttataa tgaagagcaa aaattgcgcc    9420
ataaggtgcg tccaggtata acaggatggg cgcaggtaaa tggcagaaat gctatttctt    9480
ggcagaaaaa attcgaactt gatgtgtatt atgtgaaaaa tatttctttt ttgcttgatt    9540
taaaaatcat gttttaaca gctttaaagg ttttaaaacg aagcggggta agcaagaag    9600 gccatgttac aacagagaaa tttaatggca agaactgaaa aaatttatat ttatggtgct    9660
agtggtcatg ggcttgtttg tgaagatgtg gctaaaaata tgggctataa agaatgtatt    9720
tttttagatg attttaaagg aatgaaattt gaaacacct tgcctaaata tgattttttt    9780
atagctatag gaaacaatga aattcgaaaa aagatttatc aaaaatttc agaaaatggc    9840 tttaaatag ttaatcttat tcataaagt gcacttataa gtcctagtgc aagcgtggaa    9900
gaaaatgcag ggatttaat tatgccctat gtagtgatta acgctaaagc caaaatagaa    9960
aaaggcgtga ttttaaatac ttcaagtgtg attgagcatg aatgcgtgat agggaattt   10020 tctcatgtaa gcgtaggggc taaatgtgcg ggtaatgtaa aaatcggtaa aaattgtttt   10080
ttagggatta attcttgtgt tttgcctaat ttaagcttag cagatgatag tatttttgggt   10140 ggtggagcaa ctttggttaa aagccaaaat gaaaaaggtg ttttttgtggg agtgcctgca   10200 aaagaaaaa tatgaaatga ttataaaaag attttttgttt gattctttgt aaatttttt   10260 aggtaaaata gagttaattt ataaaaattt tgttttatac aaaggataaa tcatgagatt   10320
ttttcttcct cctccgcata tgggcggtaa tgaattaaaa tatatagaag aagttttcaa   10380
aagcaattat atagcacctt tgggtgaatt tgtaaatcgc tttgagcaaa gtgtaaaaga   10440
ttatagcaaa agtgaaaatg ccttagcttt aaattcagct acagcagctt tgcatttagc   10500
tttaagggtg gcaggggtaa acaagatga tattgttttg gcttcttctt ttactttat   10560 cgcttcagtg gcgccatttt gttatcttaa agcaaaacct gtatttatag attgtgatga   10620
aacttataat atcgatgtag attttgttaaa acttgctatt aaggaatgtg aaaaaaaacc   10680
aaaagcattg atttttaactc atctttatgg caatgcggct aaaatggatg aaattgttga   10740
aatttgcaag gaaaatgaaa ttgttttaat cgaagatgct gctgaagctt taggaagttt   10800
ttataagaat aaagccttag gaacttttgg agaatttgga gcttattctt ataatggcaa   10860
taaaattatc accacttcag gtggaggtat gcttatagga aaaataaag aaaagattga   10920 aaaagcaaga tttatagca ctcaagctag ggaaaattgt ttgcattatg aacatttaga   10980
ctatggttat aattaccgtt taagcaatgt tttaggagct attggtgtag cacaaatgga   11040
```

```
ggttttagaa caaagagtgc ttaaaaaaag agaaatttat gagtggtata aagaattttt    11100
aggagagtat tttagctttt tagatgaatt agaaaattca agaagtaatc gctggttaag    11160
tacagctttg attgattttg ataaaaatga acttaatgct tgtcaaaaag atataaatat    11220
cagtcaaaaa aatattactt tgcatccaaa aatttcaaaa ctcatagaag atttgaaaaa    11280
tgaacaaata gaaacaagac cattatggaa agctatgcac actcaagaag tatttaaagg    11340
aactaaggct tatcttaatg gcaatagtga gttattttc caaaaaggaa tttgtttgcc    11400
aagtggtacg gcgatgagca aagatgatgt ttatgaaatt tcaaaactga tcttaaagag    11460
cataaaggct taaaatgatt ttttataaaa gcaaagatt agcatttttt ttaacttcag    11520
atattgtttt aattttactt agtgtttatc tggcttttc tttgagattt agtggagata    11580
ttccgagtat tttttatcat ggcatgatgg tttctgctat tattttgctt gttttaaaac    11640
tttcattttt gtttgttttt agaatttata aagtagcttg gagattttt tccctcaatg    11700 aagcaagaaa aattttatc gctttgcttt tagctgagtt ttgttttttt cttattttt    11760 attttttag tgatttttt aatccttttc caagaagtgc tattgtgata gattttgttc    11820
tttcttatat gtttataggt actttaagaa ttagcaaaag aatgcttgtg gattttaaac    11880
cttctaaaat gaaagaagaa gaaactcctt gtattgtagt aggggcaact tctaaggctt    11940
tacatttgtt aaaaggcgca aaagaaggtt ctttagggct ttttcctgtg ggcgtagttg    12000
atgcgagaaa agagcttata gggacttatt gtgataaatt tgttgtagaa gaaaaagaaa    12060
aaataaaatc ttatgtagaa caaggggtaa aaactgccat tattgctta agacttgaac    12120 aagaagagct taaaaaactt tttgaagaac ttgtagctta tggtatttgt gatgtaaaaa    12180
tatttctttt tacaagaaat gaagcaagag atattagtat agaagacttg cttgctagaa    12240
aaccaaaaga tttagacgat agtgctgtgg cggctttttt aaaagacaag gtagttttgg    12300
taagtggagc aggtggaact ataggcagtg aactttgtaa gcaatgtatt aaatttggtg    12360
ctaagcatct tattatggtt gatcatagtg agtataatct ttataagatc aatgatgatt    12420
taaatttata taagaaaaa attactccta ttttgttaag tatttagat aagcaaagtt    12480 tagatgaggt attaaaaact tataaacctg agcttatttt acatgcagcc gcttataaac    12540
atgtgcctct ttgcgaacaa aatccacatt cagcagtaat caataatatt ttaggaacca    12600
aaattttatg cgacagtgct aaagaaaata aagtagctaa atttgtgatg ataagtacag    12660
ataaagcagt acgaccaaca aatattatgg gttgcactaa gagagtttgt gagctttata    12720
ctttaagtat gagtgatgaa aattttgaag ttgcttgtgt gcgttttggt aatgtttag    12780 gttctagtgg tagtgtgata ccgaaattta agcacaaat tgccaataat gagcctttaa    12840
ctttaacaca ccctgatata gtgcgttatt ttatgcttgt ggctgaggca gtgcaacttg    12900
ttttgcaagc tggagctatc gcaaaagggg gagaactttt tgttttggat atgggtaagc    12960
ctgtgaaaat catagattta gctaaaaaaa tgcttttact ttctaatcgc aatgatttag    13020
aaattaaaat cacaggttta agaaaaggtg agaagcttta tgaagagctt ttgattgatg    13080
aaaatgatgc taaacccaa tatgagagta tttttgtagc aaagaatgag aaggttgatc    13140
ttgattggct taataaagag atagaaaatt tacaaatatg tgaagatatt tcagaggctt    13200
tattaaagat tgtacctgaa tttaaacaca ataaagaagg catataatgt atataaaga    13260 tatacaaaga tttgaagata atcgctatcg tgctagagct tatatgagtt atattttaac    13320
aagaaatcta cccaataaac ttcctgatat tcaccttgaa acgattaaaa cagctttgga    13380
```

```
taaaatagct catgaagttg ttgttttttga tgctttgtat attttagata tttcaggcat    13440
gcaaatagaa aatgcgattt ccttaaataa ggctcatgaa atagggcagg gtgaggatag    13500
aagtactcgt tcttattttt atagagctgt aaaattaaaa cgatgtgttt tgagcgatcc    13560
ttatccttcg gttttaaaca atgaactttg cgtaacagct tctataccaa tttacgatga    13620
taaaaataac ttgcttttg ttgtttgtat tgatatcaag cttgaagata ttttaaagat    13680
tattcaagca ggaaaatttg agtttgtttt tactcaattt agtcgtttgg tgtatttttg    13740
tttcgcactg gttttatttg tgattacttg tttttttattt caaaaaggtt ttttttagtct    13800 ttttgataat caagctatag gcatagaaca tatgtttgaa agtaccattg ccataactttt    13860 agctttagct atttttgatt tggcaaaaac tttgatcgaa caagaagtat taggaaggac    13920
aaaaaaagaa gaaggtggaa ttcaaaaaac catggtgaga ttttgggttt ctattatcat    13980
tgctttagct atagaagctt tgatgttggt atttaaacttt gctattggtg atctttctca    14040
gatgatttat gcgatttatc ttatcggtgg agtgagcttg cttcttttag gcttaagtgt    14100 atatttatttt acggttaagt ataaaaataa taatatttga gtaaaatttt aagtaaaaga    14160
tgatataatg ctgttttttta aaattttttta gcttgattaa taaggctaaa aagggtaaaa    14220
taaaactata aaactttga aaggacgaaa ttgtgaaatt gttagttgtt gatgacagtt    14280
ctactatgag aaggattatt aaaaataccc taacaagact tggacacgat gatgttttag    14340
aagctgagca tggcgttgaa gcttgggatt tattaactaa aaatgaagat gtaaaagttt    14400
taattacaga ttggaatatg ccagaaatga atggcttgga gttggtaaaa aaagtaagag    14460
cagagaaaaa atatgaagat atgcctatta tcatggttac aactgagggc ggaaaagctg    14520
aagtgattac tgctttaaaa gctggcgtaa ataactatat tgtaaaacct tttactccac    14580
aagttttaaa ggaaaaactt gaagatgttt taggaacagg aagtggagaa ggtgcagctg    14640
agtaa                                                                14645

<210> SEQ ID NO 11
<211> LENGTH: 31
<212> TYPE: DNA
<213> ORGANISM: artificial sequence
<220> FEATURE:
<223> OTHER INFORMATION: primer

<400> SEQUENCE: 11
ttttgcggcc gcttctacgt gttccgcttc c                                   31

<210> SEQ ID NO 12
<211> LENGTH: 31
<212> TYPE: DNA
<213> ORGANISM: artificial sequence
<220> FEATURE:
<223> OTHER INFORMATION: primer

<400> SEQUENCE: 12
ttttgcggcc gcattgcgtt gcgctcactg c                                   31

<210> SEQ ID NO 13
<211> LENGTH: 603
<212> TYPE: DNA
<213> ORGANISM: artificial sequence
<220> FEATURE:
<223> OTHER INFORMATION: transposon

<400> SEQUENCE: 13
ggccgcctag gccgcggccg cctacttcgt atagcataca ttatacgaag ttatgtctga    60
```

```
cgctcagtgg aacgacgcgt aactcacgtt aagggatttt ggtcatgatc agcacgttga    120
caattaatca tcggcatagt atatcggcat agtataatac gacaaggtga ggaactaaaa    180
catggccaag ttgaccagtg ccgttccggt gctcaccgcg cgcgacgtcg ccggagcggt    240
cgagttctgg accgaccggc tcgggttctc ccgggacttc gtggaggacg acttcgccgg    300
tgtggtccgg gacgacgtga ccctgttcat cagcgcggtc caggaccagg tggtgccgga    360
caacaccctg gcctgggtgt gggtgcgcgg cctggacgag ctgtacgccg agtggtcgga    420
ggtcgtgtcc acgaacttcc gggacgcctc cgggccggcc atgaccgaga tcggcgagca    480
gccgtggggg cggagttcg ccctgcgcga cccggccggc aactgcgtgc acttcgtggc    540
cgaggagcag gactgaataa cttcgtatag catacattat acgaagttat ggccgcctag    600
gcc                                                                  603
```

<210> SEQ ID NO 14
<211> LENGTH: 19
<212> TYPE: DNA
<213> ORGANISM: artificial sequence
<220> FEATURE:
<223> OTHER INFORMATION: primer

<400> SEQUENCE: 14
gcgctggctg gtttagttt                                                  19

<210> SEQ ID NO 15
<211> LENGTH: 18
<212> TYPE: DNA
<213> ORGANISM: artificial sequence
<220> FEATURE:
<223> OTHER INFORMATION: primer

<400> SEQUENCE: 15
cgcattcgtt ccagaggt                                                   18

<210> SEQ ID NO 16
<211> LENGTH: 20
<212> TYPE: DNA
<213> ORGANISM: artificial sequence
<220> FEATURE:
<223> OTHER INFORMATION: primer

<400> SEQUENCE: 16
gacaaggaac aggcgatcag                                                 20

<210> SEQ ID NO 17
<211> LENGTH: 20
<212> TYPE: DNA
<213> ORGANISM: artificial sequence
<220> FEATURE:
<223> OTHER INFORMATION: primer

<400> SEQUENCE: 17
tggtgatgat ggtgatggtc                                                 20

<210> SEQ ID NO 18
<211> LENGTH: 2142
<212> TYPE: DNA
<213> ORGANISM: Campylobacter jejuni

<400> SEQUENCE: 18
atgttgaaaa aagagtattt aaaaaaccct tatttagttt tgtttgcgat gattgtatta    60

```
gcttatgttt ttagtgtatt ttgcaggttt tattgggttt ggtgggcaag tgagtttaac      120 gagtatttt tcaataatca attaatgatc atttcaaacg atggctatgc ttttgctgag       180
ggcgcaagag atatgatagc aggttttcat cagcctaatg atttgagtta ttatggatct      240
tctttatcta cgcttactta ttggcttat aaaatcacac cttttctttt tgaaagtatc      300
attttatata tgagtacttt tttatcttct ttggtggtga ttcctattat tttactagct      360
aatgaataca aacgcccttt aatgggcttt gtagctgctc ttttagcaag tgtagcaaac      420
agttattata atcgcactat gagtgggtat tatgatacgg atatgctggt aattgtttta      480
cctatgttta ttttattttt tatggtaaga atgattttaa aaaagacttt ttttcattg       540 attgccttgc cattatttat aggaatttat ctttggtggt atccttcaag ttatacttta      600
aatgtagctt taattggact tttttttaatt tatacactta tttttcatag aaaagaaaag    660 atttttata tagctgtgat tttgtcttct cttactcttt caaatatagc atggttttat      720
caaagtgcca ttatagtaat acttttttgct ttatttgctt tagagcaaaa acgcttaaat    780
tttatgatta taggaatttt aggtagtgca actttgatat tttgatttt aagtggtggg     840 gttgatccca tacttatca gcttaaattt tatatttta gaagcgatga agtgcgaat      900 ttaacacagg gctttatgta tttaatgtt aatcaaacca tacaagaagt tgaaaatgta      960
gattttagcg aatttatgcg aagaattagt ggtagtgaaa ttgttttctt gttttctttg    1020
tttggttttg tatggcttt gagaaaacat aaaagtatga ttatgctttt acctatattg    1080 gtgcttggt ttttagcctt aaaaggagga cttagattta ccatttattc tgtacctgta    1140 atggcttag gatttggttt tttattgagc gagtttaagg ctatattggt taaaaaatat    1200
agccaattaa cttcaaatgt ttgtattgtt tttgcaacta ttttgacttt ggctccagta    1260
tttatccata tttacaacta taagcgcca acagtttttt ctcaaaatga agcatcatta     1320
ttaaatcaat taaaaaatat agccaataga gaagattatg tggtaacttg gtgggattat    1380
ggttatcctg tgcgttatta tagcgatgtg aaaactttag tagatggtgg aaagcattta    1440
ggtaaggata attttttccc ttcttttttct ttaagtaaag atgaacaagc tgcagctaat    1500
atggcaagac ttagtgtaga atatacagaa aaaagctttt atgctccgca aaatgatatt    1560
ttaaaatcag acatttaca agccatgatg aaagattata atcaaagcaa tgtggattta    1620
tttctagctt cattatcaaa acctgatttt aaaatcgata caccaaaaac tcgtgatatt    1680
tatctttata tgcccgctag aatgtctttg attttttcta cggtggctag ttttttctttt   1740 attaattttag atacaggagt tttggataaa ccttttacct ttagcacagc ttatccactt    1800
gatgttaaaa atggagaaat ttatcttagc aacggagtgg ttttaagcga tgattttaga    1860
agttttaaaa taggtgataa tgtggttct gtaaatagta tcgtagagat taattctatt    1920
aaacaaggtg aatacaaaat cactccaatc gatgataagg ctcagtttta tattttttat    1980
ttaaaggata gtgctattcc ttacgcacaa tttattttaa tggataaaac catgtttaat    2040
agtgcttatg tgcaaatgtt ttttttggga aattatgata gaatttatt tgacttggtg     2100 attaattcta gagatgctaa agttttaaa cttaaaattt aa                         2142
```

<210> SEQ ID NO 19
<211> LENGTH: 5
<212> TYPE: PRT
<213> ORGANISM: artificial sequence
<220> FEATURE:
<223> OTHER INFORMATION: glycosylation motif

<400> SEQUENCE: 19

Asp Val Asn Val Thr
1               5

<210> SEQ ID NO 20
<211> LENGTH: 5
<212> TYPE: PRT
<213> ORGANISM: artificial sequence
<220> FEATURE:
<223> OTHER INFORMATION: glycosylation motif

<400> SEQUENCE: 20

Glu Val Asn Ala Thr
1               5

<210> SEQ ID NO 21
<211> LENGTH: 5
<212> TYPE: PRT
<213> ORGANISM: artificial sequence
<220> FEATURE:
<223> OTHER INFORMATION: glycosylation motif

<400> SEQUENCE: 21

Asp Gln Asn Ala Thr
1               5

<210> SEQ ID NO 22
<211> LENGTH: 5
<212> TYPE: PRT
<213> ORGANISM: artificial sequence
<220> FEATURE:
<223> OTHER INFORMATION: glycosylation motif

<400> SEQUENCE: 22

Asp Asn Asn Asn Thr
1               5

<210> SEQ ID NO 23
<211> LENGTH: 5
<212> TYPE: PRT
<213> ORGANISM: artificial sequence
<220> FEATURE:
<223> OTHER INFORMATION: glycosylation motif

<400> SEQUENCE: 23

Asp Asn Asn Asn Ser
1               5

<210> SEQ ID NO 24
<211> LENGTH: 5
<212> TYPE: PRT
<213> ORGANISM: artificial sequence
<220> FEATURE:
<223> OTHER INFORMATION: glycosylation motif

<400> SEQUENCE: 24

Asp Gln Asn Arg Thr
1               5

<210> SEQ ID NO 25
<211> LENGTH: 5
<212> TYPE: PRT
<213> ORGANISM: artificial sequence
<220> FEATURE:
<223> OTHER INFORMATION: glycosylation motif

<400> SEQUENCE: 25

Glu Asn Asn Phe Thr
1               5

<210> SEQ ID NO 26
<211> LENGTH: 5
<212> TYPE: PRT
<213> ORGANISM: artificial sequence
<220> FEATURE:
<223> OTHER INFORMATION: glycosylation motif

<400> SEQUENCE: 26

Asp Ser Asn Ser Thr
1               5

<210> SEQ ID NO 27
<211> LENGTH: 5
<212> TYPE: PRT
<213> ORGANISM: artificial sequence
<220> FEATURE:
<223> OTHER INFORMATION: glycosylation motif

<400> SEQUENCE: 27

Asp Gln Asn Ile Ser
1               5

<210> SEQ ID NO 28
<211> LENGTH: 5
<212> TYPE: PRT
<213> ORGANISM: artificial sequence
<220> FEATURE:
<223> OTHER INFORMATION: glycosylation motif

<400> SEQUENCE: 28

Asp Gln Asn Val Ser
1               5

<210> SEQ ID NO 29
<211> LENGTH: 5
<212> TYPE: PRT
<213> ORGANISM: artificial sequence
<220> FEATURE:
<223> OTHER INFORMATION: glycosylation motif

<400> SEQUENCE: 29

Asp Asn Asn Val Ser
1               5

<210> SEQ ID NO 30
<211> LENGTH: 5
<212> TYPE: PRT
<213> ORGANISM: artificial sequence
<220> FEATURE:
<223> OTHER INFORMATION: glycosylation motif

<400> SEQUENCE: 30

Asp Tyr Asn Val Ser
1               5

<210> SEQ ID NO 31
<211> LENGTH: 5
<212> TYPE: PRT
<213> ORGANISM: artificial sequence
<220> FEATURE:
<223> OTHER INFORMATION: glycosylation motif

<400> SEQUENCE: 31

Asp Phe Asn Val Ser

```
<210> SEQ ID NO 32
<211> LENGTH: 5
<212> TYPE: PRT
<213> ORGANISM: artificial sequence
<220> FEATURE:
<223> OTHER INFORMATION: glycosylation motif

<400> SEQUENCE: 32

Asp Phe Asn Ala Ser
1               5

<210> SEQ ID NO 33
<211> LENGTH: 5
<212> TYPE: PRT
<213> ORGANISM: artificial sequence
<220> FEATURE:
<223> OTHER INFORMATION: glycosylation motif

<400> SEQUENCE: 33

Asp Phe Asn Ser Ser
1               5

<210> SEQ ID NO 34
<211> LENGTH: 5
<212> TYPE: PRT
<213> ORGANISM: artificial sequence
<220> FEATURE:
<223> OTHER INFORMATION: glycosylation motif

<400> SEQUENCE: 34

Asp Val Asn Ala Thr
1               5

<210> SEQ ID NO 35
<211> LENGTH: 5
<212> TYPE: PRT
<213> ORGANISM: artificial sequence
<220> FEATURE:
<223> OTHER INFORMATION: glycosylation motif

<400> SEQUENCE: 35

Asp Phe Asn Val Thr
1               5

<210> SEQ ID NO 36
<211> LENGTH: 5
<212> TYPE: PRT
<213> ORGANISM: artificial sequence
<220> FEATURE:
<223> OTHER INFORMATION: glycosylation motif

<400> SEQUENCE: 36

Asp Val Asn Ala Ser
1               5

<210> SEQ ID NO 37
<211> LENGTH: 37
<212> TYPE: DNA
<213> ORGANISM: artificial sequence
<220> FEATURE:
<223> OTHER INFORMATION: primer

<400> SEQUENCE: 37
aagaattcat gttgaaaaaa gagtatttaa aaaaccc                             37
```

<210> SEQ ID NO 38
<211> LENGTH: 62
<212> TYPE: DNA
<213> ORGANISM: artificial sequence
<220> FEATURE:
<223> OTHER INFORMATION: primer

<400> SEQUENCE: 38
aaccatggtt aagcgtaatc tggaacatcg tatgggtaaa ttttaagttt aaaaacctta      60
gc                                                                    62

<210> SEQ ID NO 39
<211> LENGTH: 47
<212> TYPE: DNA
<213> ORGANISM: Artificial Sequence
<220> FEATURE:
<223> OTHER INFORMATION: primer

<400> SEQUENCE: 39
ttttgaattc gattatcgcc atggcgtcaa atttttaattt cgctaaa                   47

<210> SEQ ID NO 40
<211> LENGTH: 41
<212> TYPE: DNA
<213> ORGANISM: Artificial Sequence
<220> FEATURE:
<223> OTHER INFORMATION: primer

<400> SEQUENCE: 40
ttttgaattc ttattttttg agtttataaa ttttagttga t                         41

<210> SEQ ID NO 41
<211> LENGTH: 13659
<212> TYPE: DNA
<213> ORGANISM: Campylobacter jejuni

<400> SEQUENCE: 41
ttactcagct gcaccttctc cacttcctgt tcctaaaaca tcttcaagtt tttcctttaa      60
aacttgtgga gtaaaaggtt ttacaatata gttatttacg ccagctttta aagcagtaat    120
cacttcagct tttccgccct cagttgtaac catgataata ggcatatctt catatttttt    180
ctctgctctt acttttttta ccaactccaa gccattcatt tctggcatat tccaatctgt    240
aattaaaact tttacatctt catttttagt taataaatcc caagcttcaa cgccatgctc    300
agcttctaaa acatcatcgt gtccaagtct tgttagggta ttttttaataa tccttctcat    360 agtagaactg tcatcaacaa ctaacaattt cacaatttcg tcctttcaaa gttttttatag    420 ttttatttta cccttttttag ccttattaat caagctaaaa aattttaaaa aacagcatta    480
tatcatcttt tacttaaatt tttactcaaa tattattatt tttatactta accgtaaata    540
aatatacact taagcctaaa agaagcaagc tcactccacc gataagataa atcgcataaa    600
tcatctgaga aagatcacca atagcaagtt taaataccaa catcaaagct tctatagcta    660
aagcaatgat aatagaaccc aaaaatctca ccatggtttt ttgaattcca ccttcttctt    720 ttttgtcct tcctaatact tcttgttcga tcaaagtttt tgccaaatca aaaatagcta    780
aagctaaagt tatggcaatg gtactttcaa acatatgttc tatgcctata gcttgattat    840 caaaagact aaaaaaacct ttttgaaata aaaacaagt aatcacaaat aaaaccagtg    900
cgaaacaaaa atacaccaaa cgactaaatt gagtaaaaac aaactcaaat tttcctgctt    960
gaataatctt taaatatctt tcaagcttga tatcaataca acaacaaaaa agcaagttat   1020

```
ttttatcatc gtaaattggt atagaagctg ttacgcaaag ttcattgttt aaaaccgaag    1080
gataaggatc gctcaaaaca catcgtttta attttacagc tctataaaaa taagaacgag    1140
tacttctatc ctcaccctgc cctatttcat gagccttatt taaggaaatc gcattttcta    1200
tttgcatgcc tgaaatatct aaaatataca aagcatcaaa acaacaact tcatgagcta     1260
ttttatccaa agctgtttta atcgtttcaa ggtgaatatc aggaagttta ttgggtagat    1320
ttcttgttaa aatataactc atataagctc tagcacgata gcgattatct tcaaatcttt    1380
gtatatcttt tatatacatt atatgccttc tttattgtgt ttaaattcag gtacaatctt    1440
taataaagcc tctgaaatat cttcacatat ttgtaaattt tctatctctt tattaagcca    1500
atcaagatca accttctcat tctttgctac aaaaatactc tcatattggg ttttagcatc    1560
attttcatca atcaaaagct cttcataaag cttctcacct tttcttaaac ctgtgatttt    1620
aatttctaaa tcattgcgat tagaaagtaa aagcattttt ttagctaaat ctatgatttt    1680
cacaggctta cccatatcca aaacaaaaag ttctccccct tttgcgatag ctccagcttg    1740
caaaacaagt tgcactgcct cagccacaag cataaaataa cgcactatat cagggtgtgt    1800
taaagttaaa ggctcattat tggcaatttg tgctttaaat ttcggtatca cactaccact    1860
agaacctaaa acattaccaa acgcacaca agcaacttca aaattttcat cactcatact     1920
taaagtataa agctcacaaa ctctcttagt gcaacccata atatttgttg gtcgtactgc    1980
tttatctgta cttatcatca caaatttagc tactttattt tctttagcac tgtcgcataa    2040
aattttggtt cctaaaatat tattgattac tgctgaatgt ggattttgtt cgcaaagagg    2100
cacatgttta taagcggctg catgtaaaat aagctcaggt ttataagttt ttaatacctc    2160
atctaaactt tgcttatcta aaatacttaa caaaatagga gtaatttttt ctttatataa    2220
atttaaatca tcattgatct tataaagatt atactcacta tgatcaacca taataagatg    2280
cttagcacca aatttaatac attgcttaca aagttcactg cctatagttc cacctgctcc    2340
acttaccaaa actaccttgt cttttaaaaa agccgccaca gcactatcgt ctaaatcttt    2400
tggttttcta gcaagcaagt cttctatact aatatctctt gcttcatttc ttgtaaaaga    2460
aaatattttt acatcacaaa taccataagc tacaagttct tcaaaaagtt ttttaagctc    2520
ttcttgttca agtcttaaag caataatggc agttttttacc ccttgttcta cataagattt    2580
tatttttttct ttttcttcta caacaaattt atcacaataa gtcccctataa gctcttttct   2640
cgcatcaact acgcccacag gaaaaagccc taaagaacct tcttttgcgc ttttaacaa     2700
atgtaaagcc ttagaagttg cccctactac aatacaagga gtttcttctt ctttcatttt    2760
agaaggttta aaatccacaa gcattctttt gctaattctt aaagtaccta taaacatata    2820
agaagaaca aaatctatca caatagcact tcttggaaaa ggattaaaaa aatcactaaa     2880
aaaataaaaa ataagaaaaa aacaaaactc agctaaaagc aaagcgataa aaattttttct   2940
tgcttcattg agggaaaaaa atctccaagc tactttataa attctaaaaa caaacaaaaa    3000
tgaaagtttt aaaacaagca aaataatagc agaaaccatc atgccatgat aaaaaatact    3060
cggaatatct ccactaaatc tcaaagaaaa agccagataa acactaagta aaattaaaac    3120
aatatctgaa gttaaaaaaa atgctaatct tttgcttttta taaaaaatca ttttaagcct    3180
ttatgctctt taagatcagt tttgaaattt cataaacatc atctttgctc atcgccgtac    3240
cacttggcaa acaaattcct ttttggaaaa ataactcact attgccatta agataagcct    3300
tagttccttt aaatacttct tgagtgtgca tagctttcca taatggtctt gtttctattt    3360
```

```
gttcatttttt caaatcttct atgagttttg aaattttggg atgcaaagta atatttttt      3420 gactgatatt tatatctttt tgacaagcat taagttcatt tttatcaaaa tcaatcaaag      3480
ctgtacttaa ccagcgatta cttcttgaat tttctaattc atctaaaaag ctaaaatact      3540
ctcctaaaaa ttctttatac cactcataaa tttctctttt tttaagcact ctttgttcta      3600
aaacctccat ttgtgctaca ccaatagctc ctaaaacatt gcttaaacgg taattataac      3660
catagtctaa atgttcataa tgcaaacaat tttccctagc ttgagtgcta taaaatcttg      3720 cttttttcaat cttttctttta tttttttccta taagcatacc tccacctgaa gtggtgataa      3780
ttttattgcc attataagaa taagctccaa attctccaaa agttcctaag gctttattct      3840
tataaaaact tcctaaagct tcagcagcat cttcgattaa aacaatttca ttttccttgc      3900
aaatttcaac aatttcatcc atttttagccg cattgccata aagatgagtt aaaatcaatg      3960
cttttggttt ttttttcacat tccttaatag caagttttaa caaatctaca tcgatattat      4020
aagtttcatc acaatctata aatacaggtt ttgctttaag ataacaaata ggcgccactg      4080
aagcgataaa agtaaaagaa gaagccaaaa caatatcatc ttgttttacc cctgccaccc      4140
ttaaagctaa atgcaaagct gctgtagctg aatttaaagc taaggcattt tcacttttgc      4200
tataatcttt tacactttgc tcaaagcgat ttacaaattc acccaaaggt gctatataat      4260
tgcttttgaa aacttcttct atatatttta attcattacc gcccatatgc ggaggagaaa      4320
gaaaaaatct catgatttat cctttgtata aaacaaaatt tttataaatt aactctattt      4380
tacctaaaaa aatttacaaa gaatcaaaca aaaatctttt tataatcatt tcatattttt      4440 cttttttgcag gcactcccac aaaaacacct ttttcatttt ggcttttaac caaagttgct      4500
ccaccaccca aaatactatc atctgctaag cttaaattag gcaaaacaca agaattaatc      4560
cctaaaaaac aattttttacc gattttttaca ttacccgcac atttagcccc tacgcttaca      4620
tgagaaaatt cccctatcac gcattcatgc tcaatcacac ttgaagtatt taaaatcacg      4680
cctttttcta ttttggcttt agcgttaatc actacatagg gcataattaa aatccctgca      4740
ttttcttcca cgcttgcact aggacttata agtgcacttt tatgaataag attaactatt      4800
ttaaagccat tttctgaaat ttttttgataa atctttttttc gaatttcatt gtttcctata      4860
gctataaaaa aatcatattt aggcaaggtg ttttcaaatt tcattccttt aaaatcatct      4920
aaaaaaatac attctttata gcccatattt ttagccacat cttcacaaac aagcccatga      4980
ccactagcac cataaatata aattttttca gttcttgcca ttaaatttct ctgttgtaac      5040
atggccttct ttgcttaccc cgcttcgttt taaaacccttt aaagctgtta aaaacatgat      5100
ttttaaatca agcaaaaaag aaatatttt cacataatac acatcaagtt cgaattttttt      5160 ctgccaagaa atagcatttc tgccatttac ctgcgcccat cctgttatac ctggacgcac      5220
cttatggcgc aattttttgct cttcattata aagggataaa tactcaacca aaagaggtct      5280
aggccccaca aaactcatat ccccttttaa aacattaaaa agttgcaaaa gctcatccaa      5340
acttaagctt ctaacaattt ttccaaaggc tttcaaacgc aattcatcgc ttaataactc      5400
acccttctca tctctttcat cgctcatggt tttaaattta taaattttaa aaatttttc      5460 atctaaccca gggcgatttt gagtgaaaat cacacttcct tgagtgattt ttaaaagtaa      5520
agcagtgatt aaaatcaccg gagaaaaaag tactaaaagc actaaagcta aaataaaatc      5580
aaaaattctt ttaaaaactt tttcatacat tcttaattac cctatcataa agttttaaat      5640
aacgctgtgc gatattattt tcatcgtatt gtaaagcatc ttgggcagca ttttttagcta      5700 aatttaatct taattttttca tcttctaata aaagtgaaat ttttttcgctt aaatccttag      5760
```

```
cattttttgt ttttgcccaa agtccatcat aagcattaga aatagcctct acacaacctt    5820
cacaatcact caccactata gccttgccac aagcttttgc ctccaaaaca cttacaggaa    5880
agccttcttt atagcttggt aaaacaaaaa tatcacaatt ttgcaaaagc tcgactatat    5940
cacttctagc acccaaataa tgcaccacac ccgagtttaa aaactccaaa ctcgcacaag    6000
aaggattttc atctcttcca ccaactaaaa caaaatttgc tttgtctttt agcatagtag    6060
cactttcata aaattctttt acacctttat gccataaagc tcttgctatc ataagaacaa    6120 taggttttttt atctatattt aaatttctcc aaaaaagctc ttttttttcc gattctatat    6180
aaataggaaa aaatttttt aaattgatcc ctacggattt tatcacacaa atttatttt    6240 ccttaagtcc taaattccgc ataaactcgg cattactttc attgacaaaa ataaattggt    6300
gtgcaaattt aaaacttaat ttataaagat tattaataac aaaacgtact aaatttgcct    6360
taaaaccttg atctatataa aaagatccca agccttctac caaagcaaaa cgataaggaa    6420
tttttgccca ttttgccgct aaaattccaa aggtattgct tttgtgtgcc gcactttgaa    6480
taagatcaag atttaaattt tttaaaacct tagcaagata aaaaaaattc tttaaaacta    6540
caaaaggatt taaactagct cttgaaaact cataaacaat tacttttaaa ccaagatctc    6600 taagttttg cgtgtattca tcttgcggca ctataacaaa aacttcatct tttctatctt    6660
ttaatgcttt tataataggc attctaaaat gataaatact tgctcctgca tgtgataaaa    6720
atcctattct cattttcaac ccttaaattt taagtttaaa aaccttagca tctctagaat    6780
taatcaccaa gtcaaataaa ttcttatcat aatttcctaa aaaaaacatt tgcacataag    6840
cactattaaa catggtttta tccattaaaa taaattgtgc gtaaggaata gcactatcct    6900
ttaaataaaa aatataaaac tgagccttat catcaattgg agtgattttg tattcacctt    6960
gtttaataga attaatctct acgatactat ttacagaaac cacattatca cctattttaa    7020
aacttctaaa atcatcgctt aaaaccactc cgttgctaag ataaatttct ccattttta    7080 catcaagtgg ataagctgtg ctaaaggtaa aaggtttatc caaaactcct gtatctaaat    7140
taataaaaga aaaactagcc accgtagaaa aaatcaaaga cattctagcg ggcatataaa    7200
gataaatatc acgagttttt ggcgtatcga ttttaaaatc aggttttgat aatgaagcta    7260
gaaacaaatc cacattgctt tgattataat cttttcatcat ggcttgcaaa atgtctgttt    7320
ttaaaatatc attttgcgga gcataaaagc tttttctgt atattctaca ctaagtcttg    7380
ccatattagc tgcagcttgt tcatctttgc ttaaagcaaa agaagggaaa aaattatcct    7440
tacctaaatg ctttccacca tctactaaag ttttcacatc gctataataa cgcacaggat    7500
aaccataatc ccaccaagtt accacataat cttctctatt ggctatattt tttaattgat    7560
ttaataatga tgcttcattt tgagaaaaaa ctgttggcgc tttatagttg taaatatgga    7620
taaatactgg agctaaagtc aaaatagttg caaaaacaat acaaacattt gaagttaatt    7680
ggctatattt tttaaccatt atagccttaa actcgctcaa taaaaaacca atcctaagg    7740 ccattacagg tacagaataa atggtaaatc taagccccc ttttaaggct aaaaacccaa    7800
gcaccaatat aggtaaagcc ataatcatac ttttatgttt tctcaaaagc catacaaaac    7860
caaacaaaga aaacaaaaaa acaatttcac taccactaat tcttcgcata aattcgctaa    7920
gatctacatt ttcaacttct tgtatggttt gattgacatt aaaatacata aagccctgcg    7980
ttaaattcgc actttcatca cttctaaaaa tataaaattt aagctgataa agtataggat    8040
caaccccacc acttaaaatc aaaaatatca aagttgcact acctaaaatt cctataatca    8100
```

```
taaaatttaa gcgttttttgc tctaaggcga ataaagcaaa aagtattact ataatggcac    8160
tttgataaaa ccatgctata tttgaaagag taagagaaga caaaatcaca gctatataaa    8220
aaatcttttc ttttctatga aaaataagtg tataaattaa aaaaagtcca attaaagcta    8280
catttaaagt ataacttgaa ggataccacc aaagataaat tcctataaat aacggcaagg    8340
caatcaatga aaaaaagtct ttttttaaaa tcattcttac cataaaaaat aaaataaaca    8400
taggcaaaac aattaccagc atatccgtat cataataccc actcatagtg cgattataat    8460
aactgtttgc tatacttgct aaaagagcag ctacaaagcc cattaaagga cgtttgtatt    8520
cgttagctag caaaatagta ggaatcacca ccaaagaaga taaaaaagta ctcatatata    8580
aaatgatact ttcaaaagaa aaaggtgtga ttttataaag ccaataagta agcgcggata    8640
aagaagatcc ataataactc aaatcattag gctgatgaaa acctgctatc atatctcttg    8700
cgccctcagc aaaagcatag ccatcatttg aaatgatcat taactgatta ttgaaaaaat    8760
actcattaaa ctcacttgcc caccaaaccc aataaaacct gcaaaataca ctaaaaacat    8820
aagctaatat aatcatcgca aacaaaacta ataagggtt ttttaaatac tcttttttca    8880
acatctttta tcctaataaa tatttcaaag catcgcgtgc aattttttact ttatcaaaag    8940 ctttagccct agttttagcc ttatttttat acgcttttct taatttatcg tcttcaagca    9000
tagtctttaa accctgaaac atggagtttt cattatctac ttctactaaa agtccaaatt    9060
catcatcgcc aaaagctct cttgcgccac ttttatgatc agtgcaaacc accgcacaag    9120
aacaagctaa gctttcaatt aaaacatttg aaaagccttc aaatacagaa gcaaaagcaa    9180
aaaattcgca tttagccatg tatttataag gattattatc aaatcctaaa agcaaaacct    9240
tttcttctaa atttaactct ttaatcaaag ctaaagctc atctttaagc acaccttcac    9300
ctaaaatcac aagcttttaaa tctgttttca atcttgcata agcacgaatt aataaagcat    9360 gattttttacc tttatcaagc ctgcctacac ttaaaataaa tttatctttt aaagctacat    9420
cttcaagagc tttttgctct atattttcta aatcgatggc attgtataaa atttcacatt    9480
tttttggatt tatactaaaa ttttgcacta aatcttctaa atttccctta gaattaggca    9540
agattaaatc agcttttggg taaagcaaag aaattaaaaa tttatttgcc aaagaattaa    9600 aattatttt cgcatacatc acacttggcg tagtgcattc attgatcaca aggcgagttt    9660
tgtttccaaa cattcttgcc attaaggcta tataattagg tcgatttaaa aaacaaatt    9720 ctgtatcaat gcctaaattt ctgcaaagtt ttttatattt taaagccaaa aaaggtagtt    9780
ttaaaaattt caaaatagga ttttcactag gttttgaaca ttctaaaaaa tgaatttgac    9840
actctggaat ttcataagaa attttatcat tcattaaaat caaatgcact tcaaatttca    9900
aacttaaaat aggcaataaa gtcgccacaa ctctttcagc accaccactt cctaaagaat    9960
aaataaaaat gcctaatttt tgcataaagc cacccgaatt tttgataatt tttcaatcat    10020
attatttgga attatactta aaatgagtaa tatcaaagca ggagcgttga ttttatact    10080 caggctttta aacaaacact tataaagagc tttataattt tttgcaagtt ttgcataata    10140
agctgccatt ttataataac tcgcacaagt ttttttataa tctttatcct tactcattct    10200
aagttcattt tctaaaattt tagcaagctc taaatatccc aaatacaccc tatgagcatt    10260
tttactcgcc cctaaagtca cgctatcttg cctaaaaatc ctataaatcc taaagccctt    10320
atggatataa aaactttttt ccttgtataa atttacccaa agcgtggctt cattgccata    10380
aaattcttca ttaaaacgct tgttttcaag tagagatttt ttaaaaacag aaaaaaactc    10440
tccgctaaat ttagccatta aaaaatcttt tttagaaatt tcactatctt tttccaagcc    10500
```

```
cttaccgcta aattccttgc ttaaatttcc ttcttttcct atcaaacaat ttccaaaaac    10560
atgagcataa ccctcatttg cttttgcat caaggtactt aaagcccag ataaaagctc     10620 atcatcatca tctaaaaaag ttacaaactc gccacttgct tgatctaagc cattgttttt    10680
attgccattt gggccttgtt tgtaattttg atttaaaaaa tacttaatgc gatcatcatc    10740 ttttgtaaa ttttgcacca cacttttagt atcatcacta gaattatcat cgcttacaat    10800
gatttctaaa tctttaaaat cttgattttg tatgctttta atagccttt ctaacaaaac    10860 ttgacgatta aaagttggca ctataacaga aagtttaggc attttaacc tcgactataa    10920 gcttaagcca ttcttctttg atgttagaaa tttcaaagtc tttacaccctt tgtttggcat   10980 tatttacaag ttcttttcta aaattttcat catttaaaac aagttcaagt tttttagcaa   11040
gtgctatttc atcatcacaa cctaccaaaa gcccatcatg attatctttg attaaatcct   11100
tagcaccatt ataataagaa cttgaaattc tacaaacctc aaaatacaaa ctttcaatta   11160
aaaccgttgg caaaccctct acaaaagaac aaaggcaaag cacttttgct ttttcataaa   11220
gagccttgac attttcaacg cgtcctaaaa aatcaacttt tattcctaaa gattttacct   11280
tgtattcaag ttcttgcctt aactctccat ctcctgctat aacaaattta taattttctt   11340
gcaaattttt atccaaatgt gctatagctt ttaaaaacat tacagggttt ttgttgtgat   11400
ctaaacgccc tataaaaga accaaattt cttttttcaaa actagaatca aaaggaattt    11460
catcgctaaa atgacaaggg tttaataaaa gcttaacct ttttacaaat ctttcataat   11520
acaccttatc actgcttcca agcacactta aagcatcaca aaaaggatag cttcccttc    11580 ttaaaaaacg ccaagtttta ggttttaaat acgcttcatt actatgctcg ctaatgatga   11640
gtggagtttt aagtcctata ttagctagaa tacaagcaat attagttgta tccaaaaaag   11700
aaataaaaac atcagcctta ctttcttta aagcctttct taaggcaaaa aatttcttaa     11760
aacgacttgc gattttatga taaagcgtgt caaatctaaa ttgttctaaa cttgtaactt   11820
taacttcatt ttcaagctta taaaaagatt ctcctgtatg aaatttaata atacttactt    11880
catgctcttt gcaaagcgca ttagctaagg ttactaaaac acgctcagcg cctcctgaat   11940
ttaaagttgc gataataaag cttattttca tcatttctcc tctttaagct taccgtgttc   12000
taaacgataa accttatcac attgcgttat cgtagaaagg cgatgtgcga taataatcat   12060
ggttttatct ttagaaattt tataaatttc atccatgatt tttgcttcac tttgagtatc   12120
aagcgcagaa gttgcttcat caagcactaa aatttcaggc tctaaataca agcccttgc   12180 tatagctatg cgttgttttt gtcccccgct taaattactc cccccatcgc ctactttgt    12240 ctgaactcct tgaggtaaat tttttataaa atgctctaaa tttgcttgtt tgataaccct    12300 attaagttttt tcttcatcaa ccgcatctcc aaaagtgata ttttagcta tgctatcatt   12360 aaaaagatag atattttgcg ggatatagcc tatttttgg cgataatttt ttgcattact   12420
tgcatttaat tcttgcttat caattaaaat ttgcccttct tttggtttta aaagtcctat    12480
gataagatct actaaggtac ttttccaca accactctcc cctataaaag cgattttttc     12540 accttttta atgtttaaat taagattttt aaataaatat ttttttccct cataaccaaa    12600
gctaagattg caaattttaa gctcttgatt aaaacttaat tttccctcgc ccaaattttc    12660
ttcttcttgt cttaaattttt gataaataat attcaaagaa gaatgataat aaagcaaatc   12720
atgataactt gtgataatac gatttgcgct tggcattaag cgataaagcg ctaaaacaaa   12780
aatagaaatc gtggataaaa tacctgaaat atcactttca tttttcaaaa ccaaaaatac    12840
```

| | | | | |
|---|---|---|---|---|
| cacgataaaa | acaagcacac | aaaagcctat | tccttcaaga | taaattctag gcaccgcagc | 12900 |
| tacgctttca | ttggtaatat | ttgctttaga | aaaagcttca | ctttgtgctt taaaaagact | 12960 |
| taatactcca | tcttctttgg | ttttaagctt | gataaattta | aaattattta aatttgtatt | 13020 |
| taaaatttcg | aagaaatttt | tcatcgcttc | ttcgcgtctt | agtcctgctt ttttaatgat | 13080 |
| agggcttaaa | attttcacta | aaataaaagc | atttaacacc | ataaaaatac ttaaaaataa | 13140 |
| agtgatttta | taattaatca | aaagcattaa | agcataaagc | aaaagcacta caaaaatttc | 13200 |
| actcatcaaa | agtaaaaatg | atgaaatcat | agtgcttaga | ttataaactt ccctgtaat | 13260 |
| ggactttaaa | atttcagatt | gattttttg | agtaaatttt | tcataattaa tatttaaaaa | 13320 |
| tttagaaaaa | accttataag | cgatcgcatg | ataacgtcct | ttagaaaatc ttgccaaaag | 13380 |
| atgaaaataa | tacgcattta | acaaagctct | aaatacataa | aaacaataa gccccactcc | 13440 |
| aaaataaaca | atgatttcaa | aaacagggat | attaagatat | tcttttaggc tgattaaata | 13500 |
| tttattacga | tcaaaataag | aaaaatcact | agccaaagtg | ataaaaggca ttaccaaaga | 13560 |
| aatcgcaaaa | gtttctataa | aagaaacaaa | tactgaaaaa | acaagcaaga aaaataaaaa | 13620 |
| attttttatct | tccttgctta | aaataaaaaa | aagtttttt | | 13659 |

<210> SEQ ID NO 42
<211> LENGTH: 2133
<212> TYPE: DNA
<213> ORGANISM: Campylobacter sputorum

<400> SEQUENCE: 42

| | | | | |
|---|---|---|---|---|
| atgagtaatt | ttaattttgc | caaatttctg | aacaagctgc | ctagactaag caaacatacc | 60 |
| atcctgatga | tcgtgctggc | ggtgtgcttt | ggcatctttt | gtcgcttta ttgggttgtg | 120 |
| tgggcgagtg | cgtatccaca | tttatttgg | aatgatgaac | tgatgatctc tacaaatgat | 180 |
| ggctatgcgt | ttgcggaagg | tacacgcgat | atgattgccg | gctttcatca gccgaatgat | 240 |
| ctgtcatatt | atggtcgttc | actgtccact | ttaagcatgt | ggctgtatag catcctgccg | 300 |
| ttttcattag | aaaccatctt | actgtatatg | tcaacgtttc | tgagtccact gctggcagtt | 360 |
| ccgttaatct | taatcggtaa | agaactgaat | gcgtctaaag | caggctttat tgcagccctg | 420 |
| ctggcagttg | tggccaatag | ctattataat | cgcaccatgt | caggctatta tgatacggat | 480 |
| atgctgaata | tcaccttacc | gatgatggtg | ttttggagca | tcacccgcct ggttcagcgc | 540 |
| aaagaacggg | ttaatctcat | ctttattcca | gtgtttatgg | ccatctatgg ttggtggtat | 600 |
| ccatcttcat | attcactgct | gctggccatg | atcggcatgt | tgtgctgta accatcgtg | 660 |
| tttgaacgct | atgaaaaact | gaattatgaa | gcaatggtgt | ttatgattct ggcaatcact | 720 |
| agctttccga | ttcagatcaa | gtttatcatc | gtgatcattc | tgtatgcgtt aatctatttt | 780 |
| tatcagcgct | ttttcgataa | aaaagttatc | tttgccttaa | tcattgcaag tagcatttgc | 840 |
| tttatttggt | taggcggctt | aaatccaatc | ctgtttccta | tcaaatttta tatctttcgc | 900 |
| gacatagcgg | attcaggcga | tacggtgttt | aaattcttca | atgtggttca gaccattcgc | 960 |
| gaaagtagcg | ccatcgattt | taatacagtt | gcgacccgca | tctcaggtca tctgattgtg | 1020 |
| tttctggtga | gcatcgtggg | ctatatcctg | tttatcaaaa | acaacaagat tttactgctg | 1080 |
| accttaccga | tcctgtttct | gggtctgatg | tcgtttaaaa | gcggcctgcg ctttacaatc | 1140 |
| tatagcgttc | ctgtaatggc | gttaggcttt | ggctattttg | tgatgtattg ctttacgaaa | 1200 |
| atcgacatca | aagatcgctt | tctgggctat | gcctttctgt | tgtggtgac ctttagtgcc | 1260 |
| ctgtatccgt | cactgaaaca | tatctatgat | tacaaggtgt | ttccagtgtt tacacatagc | 1320 |

```
gaagtggaaa gcctggatga tctgaaaaat attgccaaac gcgaagatta tgtgctgtct   1380
tggtgggatt atggctatcc gattcgctat tatagcgatg ttaaaacact gatcgatggc   1440
ggtaaacatc taggttcaga taattttgcc gtgagctttg cactgggcag cgatcagaat   1500
agtagtgcaa atatggcccg cttagaagtg aatatacgg aacgcaatta tgaagaaaaa    1560
tttggtctga atctgaaaca gatcatgaaa gattataatg caaccaatgt gaatgagttt   1620
ctgctgtctc tgaaagatgc caacctggcc ctgcctaaac agacacgcga tatatattat   1680
tatctgccgg atcgcatgat ctatatctat cctacagtgt tagcctttag tcgcctggat   1740
ctgacgacgg gccaggaatt tgcagaaccg tttttcatcg tgagcgaacg ctttagtgca   1800
accaatgata atcagatcat gttaaacaac aatgtgattc tttcatcaga tggaacaaaa   1860
ctgtcaatca atggcaatag ctattcagtt aatacttatg tagaaaccag ctacgatcag   1920
aacgaaaaac tgaatgttaa ttattttaat atcgatccga atagcaattt ttatgtgatc   1980
tttatgaaag attatctgcg catcttagtt ctggataaaa ccctgtatga tagcgcgtat   2040
atccagctgt tgtgctgga aaattatgat aaaaatctgt ttgaaccagt catcctgaat    2100
ggtagtacga aaatctataa gctgaaaaaa taa                                2133
```

<210> SEQ ID NO 43
<211> LENGTH: 710
<212> TYPE: PRT
<213> ORGANISM: Campylobacter sputorum

<400> SEQUENCE: 43

Met Ser Asn Phe Asn Phe Ala Lys Phe Leu Asn Lys Leu Pro Arg Leu
1               5                   10                  15

Ser Lys His Thr Ile Leu Met Ile Val Leu Ala Val Cys Phe Gly Ile
            20                  25                  30

Phe Cys Arg Phe Tyr Trp Val Val Trp Ala Ser Ala Tyr Pro His Phe
        35                  40                  45

Ile Trp Asn Asp Glu Leu Met Ile Ser Thr Asn Asp Gly Tyr Ala Phe
    50                  55                  60

Ala Glu Gly Thr Arg Asp Met Ile Ala Gly Phe His Gln Pro Asn Asp
65                  70                  75                  80

Leu Ser Tyr Tyr Gly Arg Ser Leu Ser Thr Leu Ser Met Trp Leu Tyr
                85                  90                  95

Ser Ile Leu Pro Phe Ser Leu Glu Thr Ile Leu Leu Tyr Met Ser Thr
            100                 105                 110

Phe Leu Ser Pro Leu Leu Ala Val Pro Leu Ile Leu Ile Gly Lys Glu
        115                 120                 125

Leu Asn Ala Ser Lys Ala Gly Phe Ile Ala Ala Leu Leu Ala Val Val
    130                 135                 140

Ala Asn Ser Tyr Tyr Asn Arg Thr Met Ser Gly Tyr Tyr Asp Thr Asp
145                 150                 155                 160

Met Leu Asn Ile Thr Leu Pro Met Met Val Phe Trp Ser Ile Thr Arg
                165                 170                 175

Leu Val Gln Arg Lys Glu Arg Val Asn Leu Ile Phe Ile Pro Val Phe
            180                 185                 190

Met Ala Ile Tyr Gly Trp Trp Tyr Pro Ser Ser Tyr Ser Leu Leu Leu
        195                 200                 205

Ala Met Ile Gly Met Phe Val Leu Tyr Thr Ile Val Phe Glu Arg Tyr
    210                 215                 220

-continued

Glu Lys Leu Asn Tyr Glu Ala Met Val Phe Met Ile Leu Ala Ile Thr
225                 230                 235                 240

Ser Phe Pro Ile Gln Ile Lys Phe Ile Ile Val Ile Ile Leu Tyr Ala
            245                 250                 255

Leu Ile Tyr Phe Tyr Gln Arg Phe Phe Asp Lys Lys Val Ile Phe Ala
        260                 265                 270

Leu Ile Ile Ala Ser Ser Ile Cys Phe Ile Trp Leu Gly Gly Leu Asn
    275                 280                 285

Pro Ile Leu Phe Pro Ile Lys Phe Tyr Ile Phe Arg Asp Ile Ala Asp
290                 295                 300

Ser Gly Asp Thr Val Phe Lys Phe Phe Asn Val Val Gln Thr Ile Arg
305                 310                 315                 320

Glu Ser Ser Ala Ile Asp Phe Asn Thr Val Ala Thr Arg Ile Ser Gly
            325                 330                 335

His Leu Ile Val Phe Leu Val Ser Ile Val Gly Tyr Ile Leu Phe Ile
        340                 345                 350

Lys Asn Asn Lys Ile Leu Leu Leu Thr Leu Pro Ile Leu Phe Leu Gly
    355                 360                 365

Leu Met Ser Phe Lys Ser Gly Leu Arg Phe Thr Ile Tyr Ser Val Pro
370                 375                 380

Val Met Ala Leu Gly Phe Gly Tyr Phe Val Met Tyr Cys Phe Thr Lys
385                 390                 395                 400

Ile Asp Ile Lys Asp Arg Phe Leu Gly Tyr Ala Phe Leu Phe Val Val
            405                 410                 415

Thr Phe Ser Ala Leu Tyr Pro Ser Leu Lys His Ile Tyr Asp Tyr Lys
        420                 425                 430

Val Phe Pro Val Phe Thr His Ser Glu Val Glu Ser Leu Asp Asp Leu
    435                 440                 445

Lys Asn Ile Ala Lys Arg Glu Asp Tyr Val Leu Ser Trp Trp Asp Tyr
450                 455                 460

Gly Tyr Pro Ile Arg Tyr Tyr Ser Asp Val Lys Thr Leu Ile Asp Gly
465                 470                 475                 480

Gly Lys His Leu Gly Ser Asp Asn Phe Ala Val Ser Phe Ala Leu Gly
            485                 490                 495

Ser Asp Gln Asn Ser Ser Ala Asn Met Ala Arg Leu Glu Val Glu Tyr
        500                 505                 510

Thr Glu Arg Asn Tyr Glu Glu Lys Phe Gly Leu Asn Leu Lys Gln Ile
    515                 520                 525

Met Lys Asp Tyr Asn Ala Thr Asn Val Asn Glu Phe Leu Leu Ser Leu
530                 535                 540

Lys Asp Ala Asn Leu Ala Leu Pro Lys Gln Thr Arg Asp Ile Tyr Tyr
545                 550                 555                 560

Tyr Leu Pro Asp Arg Met Ile Tyr Ile Tyr Pro Thr Val Leu Ala Phe
            565                 570                 575

Ser Arg Leu Asp Leu Thr Thr Gly Gln Glu Phe Ala Glu Pro Phe Phe
        580                 585                 590

Ile Val Ser Glu Arg Phe Ser Ala Thr Asn Asp Asn Gln Ile Met Leu
    595                 600                 605

Asn Asn Asn Val Ile Leu Ser Ser Asp Gly Thr Lys Leu Ser Ile Asn
610                 615                 620

Gly Asn Ser Tyr Ser Val Asn Thr Tyr Val Glu Thr Ser Tyr Asp Gln
625                 630                 635                 640

Asn Glu Lys Leu Asn Val Asn Tyr Phe Asn Ile Asp Pro Asn Ser Asn

|   |   | 645 |   |   |   | 650 |   |   |   | 655 |   |
|---|---|---|---|---|---|---|---|---|---|---|---|

Phe Tyr Val Ile Phe Met Lys Asp Tyr Leu Arg Ile Leu Val Leu Asp
        660                  665                670

Lys Thr Leu Tyr Asp Ser Ala Tyr Ile Gln Leu Phe Val Leu Glu Asn
   675                     680                    685

Tyr Asp Lys Asn Leu Phe Glu Pro Val Ile Leu Asn Gly Ser Thr Lys
 690                   695                   700

Ile Tyr Lys Leu Lys Lys
705               710

<210> SEQ ID NO 44
<211> LENGTH: 2142
<212> TYPE: DNA
<213> ORGANISM: Campylobacter jejuni

<400> SEQUENCE: 44

| | | | | |
|---|---|---|---|---|
| atgttgaaaa | aagagtattt | aaaaaaccct | tatttagttt | tgtttgcgat | gattatatta | 60 |
| gcttatgttt | ttagtgtatt | ttgcaggttt | tattgggttt | ggtgggcaag | tgagtttaat | 120 |
| gagtatttt | tcaataatca | gttaatgatc | atttcaaatg | atggctatgc | ttttgctgag | 180 |
| ggcgcaagag | atatgatagc | aggttttcat | cagcctaatg | atttgagtta | ttatggacgt | 240 |
| tctttatccg | cgcttactta | ttggctttat | aaaatcacac | cttttctctt | tgaaagtatc | 300 |
| attttatata | tgagtacttt | tttatcttct | ttggtggtga | ttcctactat | tttgctagct | 360 |
| aacgaataca | aacgtccttt | aatgggcttt | gtagctgctc | ttttagcaag | tatagcaaac | 420 |
| agttattata | atcgcactat | gagtgggtat | tatgatacgg | atatgctggt | aattgttttg | 480 |
| cctatgttta | ttttattttt | tatggtaaga | atgattttaa | aaaagacttt | ttttcattg | 540 |
| attgccttgc | cgttatttat | aggaatttat | ctttggtggt | atccttcaag | ttatacttta | 600 |
| aatgtagctt | taattggact | ttttttaatt | tatacactta | tttttcatag | aaaagaaaag | 660 |
| attttttata | tagctgtgat | tttgtcttct | cttactcttt | caaatatagc | atggttttat | 720 |
| caaagtgcca | ttatagtaat | acttttttgct | ttattcgcct | tagagcaaaa | acgcttaaat | 780 |
| tttatgatta | taggaatttt | taggtagtgca | actttgatat | tttgattttt | aagtggtggg | 840 |
| gttgatccta | tactttatcc | gcttaaattt | tatatttta | gaagtgatga | aagtgcgaat | 900 |
| ttaacgcagg | gctttatgta | ttttaatgtc | gttcaaacca | tacaagaagt | tgaaaatgta | 960 |
| gatcttagcg | aatttatgcg | aagaattagt | ggtagtgaaa | ttgttttttt | gttttctttg | 1020 |
| tttggttttg | tatggctttt | gagaaaacat | aaaagtatga | ttatggcttt | acctatattg | 1080 |
| gtgcttgggt | ttttagcctt | aaaagggggg | cttagattta | ccatttattc | tgtacctgta | 1140 |
| atggccttag | gatttggttt | tttattgagc | gagtttaagg | ctataatggt | taaaaaatat | 1200 |
| agccaattaa | cttcaaatgt | tgtattgtt | tttgcaacta | ttttgacttt | agctccagta | 1260 |
| tttatccata | tttacaacta | taaagcgcca | acagtttttt | ctcaaaatga | agcatcatta | 1320 |
| ttaaatcaat | taaaaaatat | agccaataga | gaagattatg | tggtaacttg | gtgggattat | 1380 |
| ggttatcctg | tgcgttatta | tagcgatgtg | aaaactttag | tagatggtgg | aaagcattta | 1440 |
| ggtaaggata | attttttccc | ttcttttgct | ttaagcaaag | atgaacaagc | tgcagctaat | 1500 |
| atggcaagac | ttagtgtaga | atatacagaa | aaaagctttt | atgctccgca | aaatgatatt | 1560 |
| ttaaaaacag | acattttgca | agccatgatg | aaagattata | atcaaagcaa | tgtggatttg | 1620 |
| tttctagctt | cattatcaaa | acctgatttt | aaaatcgata | cgccaaaaac | tcgtgatatt | 1680 |
| tatctttata | tgcccgctag | aatgtctttg | atttttttcta | cggtggctag | ttttttcttttt | 1740 |

-continued

```
attaatttag atacaggagt tttggataaa cctttaccct ttagcacagc ttatccactt    1800
gatgttaaaa atggagaaat ttatcttagc aacggagtgg ttttaagcga tgattttaga    1860
agttttaaaa taggtgataa tgtggtttct gtaaatagta tcgtagagat taattctatt    1920
aaacaaggtg aatacaaaat cactccaatt gatgataagg ctcagtttta tatttttat    1980 ttaaaggata gtgctattcc ttacgcacaa tttattttaa tggataaaac catgtttaat    2040
agtgcttatg tgcaaatgtt ttttttagga aattatgata agaatttatt tgacttggtg    2100
attaattcta gagatgctaa ggttttaaa cttaaaattt aa                        2142
```

<210> SEQ ID NO 45
<211> LENGTH: 713
<212> TYPE: PRT
<213> ORGANISM: Campylobacter jejuni

<400> SEQUENCE: 45

```
Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Arg
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Ala Asn Glu Tyr Lys Arg Pro Leu Met
        115                 120                 125

Gly Phe Val Ala Ala Leu Leu Ala Ser Ile Ala Asn Ser Tyr Tyr Asn
    130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
        195                 200                 205

Leu Ile Tyr Thr Leu Ile Phe His Arg Lys Glu Lys Ile Phe Tyr Ile
    210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Pro Leu
        275                 280                 285

Lys Phe Tyr Ile Phe Arg Ser Asp Glu Ser Ala Asn Leu Thr Gln Gly
    290                 295                 300
```

```
Phe Met Tyr Phe Asn Val Val Gln Thr Ile Gln Glu Val Glu Asn Val
305                 310                 315                 320

Asp Leu Ser Glu Phe Met Arg Arg Ile Ser Gly Ser Glu Ile Val Phe
            325                 330                 335

Leu Phe Ser Leu Phe Gly Phe Val Trp Leu Leu Arg Lys His Lys Ser
        340                 345                 350

Met Ile Met Ala Leu Pro Ile Leu Val Leu Gly Phe Leu Ala Leu Lys
            355                 360                 365

Gly Gly Leu Arg Phe Thr Ile Tyr Ser Val Pro Val Met Ala Leu Gly
        370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
            405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
            435                 440                 445

Asn Arg Glu Asp Tyr Val Val Thr Trp Trp Asp Tyr Gly Tyr Pro Val
450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Thr Asp Ile Leu Gln Ala
            515                 520                 525

Met Met Lys Asp Tyr Asn Gln Ser Asn Val Asp Leu Phe Leu Ala Ser
            530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
            595                 600                 605

Leu Ser Asn Gly Val Val Leu Ser Asp Asp Phe Arg Ser Phe Lys Ile
            610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
            675                 680                 685

Leu Gly Asn Tyr Asp Lys Asn Leu Phe Asp Leu Val Ile Asn Ser Arg
            690                 695                 700

Asp Ala Lys Val Phe Lys Leu Lys Ile
705                 710
```

```
<210> SEQ ID NO 46
<211> LENGTH: 5
<212> TYPE: PRT
<213> ORGANISM: Artificial Sequence
<220> FEATURE:
<223> OTHER INFORMATION: synthetic peptide sequence
<220> FEATURE:
<221> NAME/KEY: MISC_FEATURE
<222> LOCATION: (1)..(1)
<223> OTHER INFORMATION: X is Aspartic acid or glutamic acid
<220> FEATURE:
<221> NAME/KEY: MISC_FEATURE
<222> LOCATION: (2)..(2)
<223> OTHER INFORMATION: X is any amino acid except proline
<220> FEATURE:
<221> NAME/KEY: MISC_FEATURE
<222> LOCATION: (4)..(4)
<223> OTHER INFORMATION: X is any amino acid except proline
<220> FEATURE:
<221> NAME/KEY: MISC_FEATURE
<222> LOCATION: (5)..(5)
<223> OTHER INFORMATION: X is serine or threonine

<400> SEQUENCE: 46

Xaa Xaa Asn Xaa Xaa
1               5

<210> SEQ ID NO 47
<211> LENGTH: 50
<212> TYPE: DNA
<213> ORGANISM: Artificial Sequence
<220> FEATURE:
<223> OTHER INFORMATION: Vector and C. sputorum pglB sequence

<400> SEQUENCE: 47
atttcacaca ggaaacagaa ttcatggcgt caaattttaa tttcgctaaa            50

<210> SEQ ID NO 48
<211> LENGTH: 27
<212> TYPE: DNA
<213> ORGANISM: Campylobacter sputorum

<400> SEQUENCE: 48
atggcgtcaa attttaattt cgctaaa                                     27

<210> SEQ ID NO 49
<211> LENGTH: 60
<212> TYPE: DNA
<213> ORGANISM: Artificial Sequence
<220> FEATURE:
<223> OTHER INFORMATION: Vector and C. sputorum pglB sequence

<400> SEQUENCE: 49
atttcacaca ggaaacagaa ttcgattatc gccatggcgt caaattttaa tttcgctaaa    60
```